US008053587B2

(12) United States Patent
Klemarczyk et al.

(10) Patent No.: US 8,053,587 B2
(45) Date of Patent: Nov. 8, 2011

(54) REWORKABLE THERMOSETTING RESIN COMPOSITION

(75) Inventors: Philip T. Klemarczyk, Canton, CT (US); Andrew D. Messana, Newington, CT (US); Afranio Torres-Filho, Enfield, CT (US); Erin K. Yeager, Tolland, CT (US); Takahisa Doba, Kanagawa (JP)

(73) Assignee: Henkel Corporation, Rocky Hill, CT (US)

( * ) Notice: Subject to any disclaimer, the term of this patent is extended or adjusted under 35 U.S.C. 154(b) by 729 days.

(21) Appl. No.: 12/004,343

(22) Filed: Dec. 20, 2007

(65) Prior Publication Data

US 2008/0214840 A1    Sep. 4, 2008

Related U.S. Application Data

(60) Continuation of application No. 11/007,754, filed on Dec. 8, 2004, now abandoned, which is a division of application No. 10/182,450, filed as application No. PCT/US2001/08624 on Mar. 27, 2001, now Pat. No. 7,012,120.

(60) Provisional application No. 60/193,542, filed on Mar. 31, 2000.

(51) Int. Cl.
C07D 303/04    (2006.01)
C07D 331/02    (2006.01)

(52) U.S. Cl. ............................................. 549/545; 549/1
(58) Field of Classification Search ............... 549/1, 545
See application file for complete search history.

(56) References Cited

U.S. PATENT DOCUMENTS

| | | | |
|---|---|---|---|
| 3,187,018 A | 6/1965 | Tinsley et al. | 549/545 |
| 3,299,168 A | 1/1967 | Payne | 525/523 |
| 3,378,522 A | 4/1968 | Martin | 260/47 |
| 3,658,750 A | 4/1972 | Tsukui et al. | 523/220 |
| 4,379,728 A | 4/1983 | Lin | 156/307.3 |
| 4,663,085 A | 5/1987 | Enda et al. | 427/82 |
| 4,663,190 A | 5/1987 | Fujita et al. | 427/82 |
| 4,954,580 A | 9/1990 | Zahir | 525/476 |
| 5,288,820 A | 2/1994 | Rector, Jr. et al. | 525/510 |
| 5,355,580 A | 10/1994 | Tsukada | 29/840 |
| 5,367,006 A | 11/1994 | Hermansen et al. | 523/428 |
| 5,423,931 A | 6/1995 | Inoue et al. | 156/94 |
| 5,512,613 A | 4/1996 | Afzali-Ardakani et al. | 523/443 |
| 5,560,934 A | 10/1996 | Afzali-Ardakani et al. | 424/497 |
| 5,726,391 A | 3/1998 | Iyer et al. | 174/52.2 |
| 5,760,337 A | 6/1998 | Iyer et al. | 174/52.2 |
| 5,783,867 A | 7/1998 | Belke, Jr. et al. | 257/783 |
| 5,855,821 A | 1/1999 | Chau et al. | 252/514 |
| 5,863,970 A | 1/1999 | Ghoshal et al. | 523/434 |
| 5,872,158 A | 2/1999 | Kuczynski | 522/182 |
| 5,932,682 A | 8/1999 | Buchwalter et al. | 528/94 |
| 5,948,922 A | 9/1999 | Ober et al. | 549/547 |
| 5,973,033 A | 10/1999 | Ober et al. | 523/443 |
| 6,008,266 A | 12/1999 | Kuczynski et al. | 522/31 |
| 6,617,401 B2 | 9/2003 | Rubinsztajn | 525/533 |
| 6,627,683 B1 | 9/2003 | Klemarczyk et al. | 523/457 |
| 6,887,737 B1 | 5/2005 | Woods et al. | 483/106 |

FOREIGN PATENT DOCUMENTS

| | | |
|---|---|---|
| GB | 1305702 | 7/1973 |
| GB | 1503213 | 3/1978 |
| JP | 58-42290 | 3/1983 |
| JP | 58-8715 | 1/1984 |
| JP | 59-27945 | 2/1984 |
| JP | 59-197426 | 11/1984 |
| JP | 60-11525 A | 1/1985 |
| JP | 62-295029 | 6/1986 |
| JP | 61-143420 A | 7/1986 |
| JP | 63-159426 | 12/1986 |
| JP | 63-23922 | 2/1988 |
| JP | 2-18412 | 1/1990 |
| JP | 4-202523 | 7/1992 |
| JP | 5-102343 | 4/1993 |
| JP | 5-251516 | 9/1993 |
| JP | 5-271389 | 10/1993 |
| JP | 6-77264 | 3/1994 |
| JP | 06069280 | 3/1994 |
| JP | 6928094 | 3/1994 |
| JP | 6-136092 | 5/1994 |
| JP | 6-184409 | 5/1994 |
| JP | 8-12741 | 1/1996 |
| JP | 9-316421 | 9/1997 |
| JP | 9-279121 | 10/1997 |
| JP | 10-175979 | 6/1998 |
| JP | 10-231351 | 9/1998 |
| JP | 11-12440 | 1/1999 |
| JP | 11-17074 | 1/1999 |
| JP | 11-209689 | 3/1999 |
| JP | 11-106481 | 4/1999 |
| JP | 11-140161 | 5/1999 |
| JP | 11-279519 | 10/1999 |
| JP | 11-302507 | 11/1999 |
| WO | WO 85/02184 A | 5/1985 |

(Continued)

OTHER PUBLICATIONS

Sergeev et al., "Diglycidyl Aromatic Thio Ethers and Epoxy Polymers Derived from Them", Vysokomol. Soedin., Ser. A (1984) 26(1), 208-11.
Crivello et al., "Structure and Reactivity Relationships in Photinitiated Cationic Polymerization of Oxetane Monomers" J. Macromol. Sci., Pure Appl. Chem., vol. A30, No. 2-3, 189-206. (1993).
Chemical abstracts registry No. 1978:74846 for the Kunstoffe article by Pilny, 1977 vol. 67 No. 12, Abstract, one page.
Buchwalter et al., "Cleavable Epoxy Resins: Design for Disassembly of a Thermoset", Thomas Watson Research Center, Journal of Polymer Science: Part A: Polymer Chemistry, vol. 34, 249-260 (1996).
Wang et al., "Novel Thermally Reworkable Underfill Encapsulants for Flip-Chip Applications", School of Material Science and Engineering, Georgia Institute of Technology, Electric Components and Technology Conference, 92-100 (1998).

(Continued)

*Primary Examiner* — Bernard Dentz
(74) *Attorney, Agent, or Firm* — Steven C. Bauman

(57) ABSTRACT

This invention relates to thermosetting resin compositions useful for mounting onto a circuit board semiconductor devices, such as CSPs, BGAs, LGAs and the like, each of which having a semiconductor chip, such as LSI, on a carrier substrate. The compositions of this invention are reworkable when subjected to appropriate conditions.

2 Claims, 18 Drawing Sheets

FOREIGN PATENT DOCUMENTS

| WO | 94/20580 | 9/1994 |
|---|---|---|
| WO | WO 98/06007 A | 2/1998 |
| WO | WO 98/31738 A | 7/1998 |
| WO | WO 99/05196 A | 2/1999 |
| WO | 99/35187 | 7/1999 |
| WO | 99/56799 | 8/2000 |

OTHER PUBLICATIONS

Chemical abstracts registry No. 96-08-2 for limonene diepoxide, 1967.
Chemical abstract registry No. 127-41-3 for alpha-ionene, 1967.
Chemical abstract registry No. 472-93-5 for gamma-carotene, 1967.
Chemical abstract registry No. 14901-07-6 for 4-(2,6,6-trimethyl-1-cyclohexenyl)-3-buten-2-one, 1967.

REWORKABLE THERMOSETTING RESIN COMPOSITION

This application is a continuation of U.S. patent application Ser. No. 11/007,754, filed Dec. 8, 2004, now abandoned which is a divisional of U.S. patent application Ser. No. 10/182,450 filed Jul. 29, 2002, now. U.S. Pat. No. 7,012,120, which claims the benefit of International Patent Application No. PCT/US2001/08624 filed Mar. 27, 2001 and published on Oct. 11, 2001 as WO 01/74798 which claims the benefit of U.S. Provisional Patent Application No. 61/193,542 filed Mar. 31, 2000, the contents of each of which are incorporated herein by reference in their entirety.

BACKGROUND OF THE INVENTION

1. Field of the Invention

This invention relates to thermosetting resin compositions useful for instance, in mounting onto a circuit board semiconductor devices, such as chip size or chip scale packages ("CSPs"), ball grid arrays ("BGAs"), land grid arrays ("LGAs") and the like, each of which having a semiconductor chip, such as large scale integration ("LSI"), on a carrier substrate. The compositions of this invention are reworkable when subjected to appropriate conditions.

2. Brief Description of Related Technology

In recent years, the popularity of small-sized electronic appliances, such as camera-integrated video tape recorders ("VTRs") and portable telephone sets, has made size reduction of LSI devices desirable. As a result, CSPs, BGAs and LGAs are being used to reduce the size of packages substantially to that of bare chips. Such CSPs, BGAs, LGAs improve the characteristics of the electronic device while retaining many of their operating features, thus serving to protect semiconductor bare chips, such as LSIs, and facilitate testing thereof.

Ordinarily, the CSP/BGA/LGA assembly is connected to electrical conductors on a circuit board by use of a solder connection or the like. However, when the resulting CSP/BGA/LGA/circuit board structure is exposed to thermal cycling, the reliability of the solder connection between the circuit board and the CSP/BGA/LGA often becomes suspect. Recently, after a CSP/BGA/LGA assembly is mounted on a circuit board, the space between the CSP/BGA/LGA assembly and the circuit board is often now filled with a sealing resin (often referred to as underfill sealing) in order to relieve stresses caused by thermal cycling, thereby improving heat shock properties and enhancing the reliability of the structure.

However, since thermosetting resins are typically used as the underfill sealing material, in the event of a failure after the CSP/BGA/LGA assembly is mounted on the circuit board, it is very difficult to replace the CSP/BGA/LGA assembly without destroying or scrapping the structure in its entirety.

To that end, techniques for mounting a bare chip on a circuit board are accepted as substantially similar to the mounting of a CSP/BGA/LGA assembly onto a circuit board. One such technique, disclosed in Japanese Laid-Open Patent Publication No. 102343/93, involves a mounting process where a bare chip is fixed and connected to a circuit board by use of a photocurable adhesive, where, in the event of failure, this bare chip is removed therefrom. However, this technique is limited to those instances where the circuit board includes a transparent substrate (e.g., glass) which permits exposure to light from the back side, and the resulting structure exhibits poor heat shock properties.

Japanese Laid-Open Patent Publication No. 69280/94 discloses a process where a bare chip is fixed and connected to a substrate by use of a resin capable of hardening at a predetermined temperature. In the event of failure, this bare chip is removed from the substrate by softening the resin at a temperature higher than the predetermined temperature. However, no specific resin is disclosed, and there is no disclosure about treating the resin which remains on the substrate. Thus, the disclosed process is at best incomplete.

As pointed out in Japanese Laid-Open Patent Publication No. 77264/94, it is conventional to use a solvent to remove residual resin from a circuit board. However, swelling the resin with a solvent is a time consuming process and the corrosive organic acid ordinarily used as the solvent may reduce the reliability of the circuit board. Instead, that disclosure speaks to a method for removing residual resin by irradiation with electromagnetic radiation.

Japanese Laid-Open Patent Publication No. 251516/93 also discloses a mounting process using bisphenol A type epoxy resin (CV5183 or CV5183S; manufactured by Matsushita Electric Industrial Co., Ltd.). However, the removal process so disclosed does not consistently permit easy removal of the chip, the curing step is lengthy at elevated temperatures, and the process generally results in poor productivity.

Of course, mechanical methods of removing/replacing semiconductor chips from/on a substrate are known, such as by cutting the chip to be removed/replaced. See U.S. Pat. No. 5,355,580 (Tsukada).

Thermoplastic underfill resins are known for use in semiconductor chip attachment. See U.S. Pat. No. 5,783,867 (Belke, Jr.). However, such thermoplastic resins tend to leak under relatively modest temperature conditions. In contrast, thermosetting resins cure into a matrix which ordinarily have greater thermal stability under end use operating temperatures.

U.S. Pat. Nos. 5,512,613 (Afzali-Ardakani), 5,560,934 (Afzali-Ardakani) and 5,932,682 (Buchwalter), each refer to a reworkable thermoset composition based on a diepoxide component in which the organic linking moiety connecting the two epoxy groups of the diepoxide includes an acid cleavable acyclic acetal group. With such acid cleavable acyclic acetal groups forming the bases of the reworkable composition, a cured thermoset need only be introduced to an acidic environment in order to achieve softening and a loss of much of its adhesiveness.

U.S. Pat. No. 5,872,158 (Kuczynski) and 6,008,266 (Kuczynski), each refer to thermosetting compositions capable of curing upon exposure to actinic radiation, which are based on acetal diacrylates and acetal diepoxides, respectively, and reaction products of which are reported to be soluble in dilute acid.

U.S. Pat. No. 5,760,337 (Iyer) refers to thermally reworkable crosslinked resins to fill the gap created between a semiconductor device and a substrate to which it is attached. These resins are produced by reacting a dienophile (with a functionality greater than 1) with a 2.5-dialkyl substituted furan-containing polymer.

International Patent Publication No. PCT/US98/00858 refers to a thermosetting resin composition capable of sealing underfilling between a semiconductor device including a semiconductor chip mounted on a carrier substrate and a circuit board to which said semiconductor device is electrically connected. The composition includes about 100 parts by weight of an epoxy resin, about 3 to about 60 parts by weight of a curing agent, and about 1 to about 90 parts by weight of a plasticizer. Here, the area around the cured thermoset is to be heated at a temperature of about 190 to about 260° C. for a period of time ranging from about 10 seconds to about 1 minute in order to achieve softening and a loss of much of its adhesiveness.

U.S. Pat. Nos. 5,948,922 (Ober) and 5,973,033 (Ober), each refer to a certain class of compounds having tertiary oxycarbonyl linkages, and compositions based on such compounds, which when cured provide thermally decomposable compositions capable of being reworked.

Notwithstanding the state of the art, it would be desirable for an underfilling sealing material to provide good productivity, thermal shock and mechanical stress absorbing properties, while allowing the substrates with which it is to be used to be readily processed and easily separated from a semiconductor device without application of too extreme conditions that may compromise the integrity of the semiconductor devices remaining on the substrate or the substrate itself. In addition, it would be desirable to provide such a material which is based on an epoxy material for reworkability that may be prepared from readily available and inexpensive starting materials.

SUMMARY OF THE INVENTION

The present invention provides a thermosetting resin composition, which includes broadly a curable resin component, at least a portion of which is a compound having at least one linkage selected from oxiranes, thiiranes, and combinations thereof, substituted on at least three of the substitutable positions on the oxirane and/or thiirane carbons, respectively, with an alkyl, alkenyl or aryl substituent having a carbon content of one to about twelve carbon atoms, with or without substitution or interruption by one or more heteroatoms or halogens, as appropriate; and a curing agent component including an anhydride component, a nitrogen-containing component, such as amine or aza compounds, amide compounds, and/or imidazole compounds, or combinations thereof.

The present invention also provides novel diepoxide-containing compounds, the structures for which are described in detail herein.

Reaction products of these compositions are capable of softening under exposure to elevated temperature conditions, such as in excess of the temperatures used to cure the composition. Such temperature exposure provides the reworkable aspect of the reaction products of the inventive compositions. The remaining components, discussed below, provide the physical properties and characteristics for the compositions and reaction products to render the compositions attractive for commercial use, particularly in the microelectronics industry.

The inventive compositions are useful as an underfilling sealing resin, and enables a semiconductor device, such as a CSP/BGA/LGA assembly which includes a semiconductor chip mounted on a carrier substrate, to be securely connected to a circuit board by short-time heat curing and with good productivity. Reaction products of the inventive compositions demonstrate excellent heat shock properties, and permit the semiconductor device to be easily removed from the circuit board by localized heating in excess of the temperature at which the composition cures, in the event of semiconductor device or connection failure. This makes it possible to reuse the circuit board (with the remaining functioning semiconductor devices still electrically attached) and thereby achieve an improvement in the yield of the production process and a reduction in production cost.

The compositions of this invention may also be used for microelectronic applications beyond sealing underfill, such as with glob top, die attachment and other applications for thermosetting compositions.

Other benefits and advantages of the present invention will become more readily apparent after a reading of the "Detailed Description" section together with the figures.

DETAILED DESCRIPTION OF THE INVENTION

Figure 1:
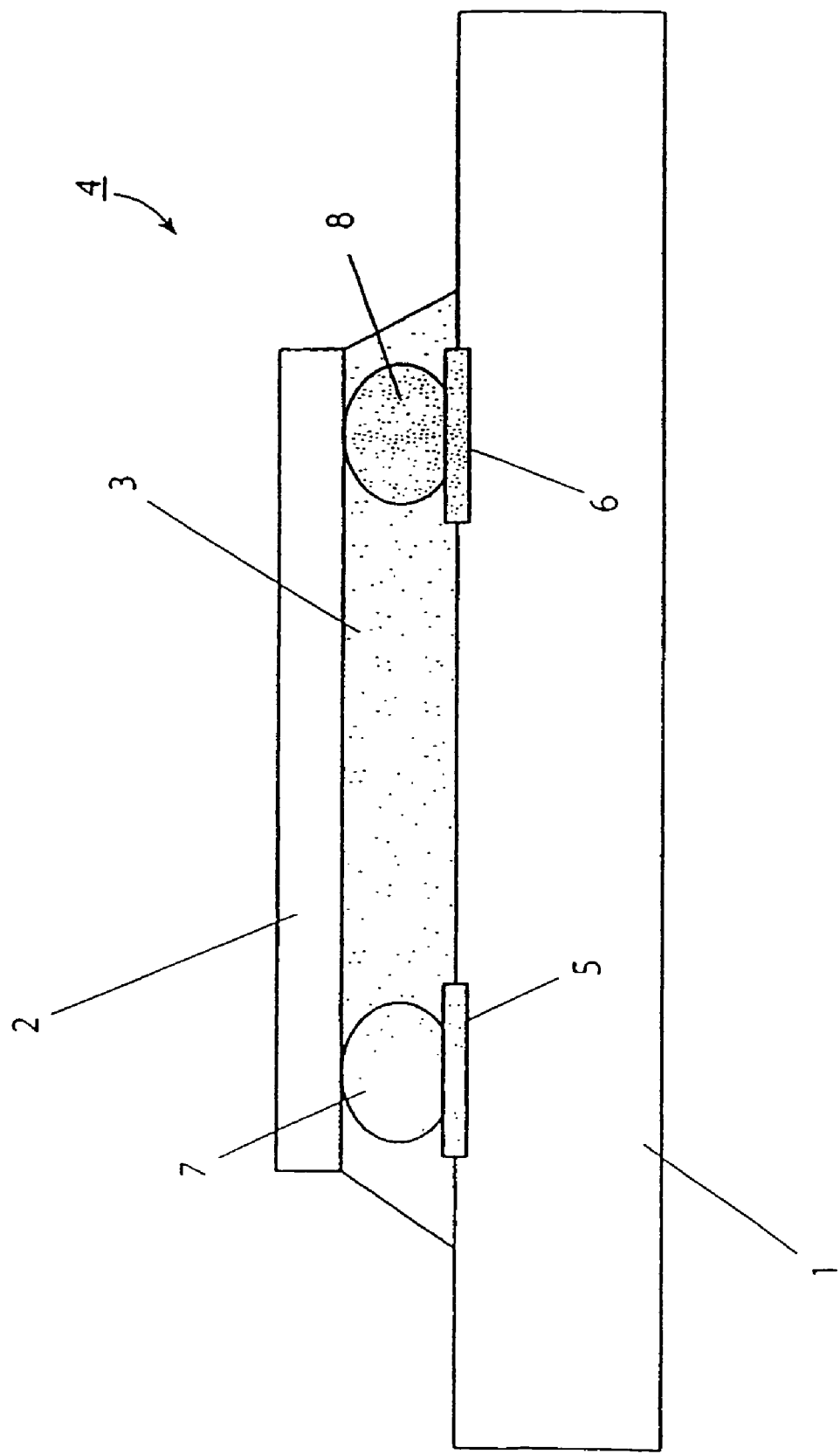
FIG. 1 depicts a cross-sectional view showing an example of the mounting structure in which the thermosetting resin composition of the present invention is used.

As noted above, the thermosetting resin compositions are useful for instance in microelectronic assembly applications, such as underfill sealants between a semiconductor device and a circuit board to which the semiconductor device is electrically connected. Of course, the compositions may also be used for other microelectronic assembly applications, such as the direct chip attach applications, including glob top, and dam and fill. In addition, the compositions may be used in far-flung applications, where thermosetting epoxies, or for that matter other thermosetting or thermoplastic adhesive, coating and sealant compositions, may be used.

For instance, the compositions may be used in the assembly of products, whose component parts have value as do the intermediate/finished products, to facilitate assembly and disassembly thereof where defective component parts are found. In that event, the defective component part(s) may be readily removed from the intermediate/finished product(s) and be replaced without having to scrap the entire intermediate/finished product(s). In addition, the speed with which the disassembly may proceed allows throughput to remain high. A non-microelectronic example of such a part is the assembly of prosthetic devices.

The composition includes broadly (a) an epoxy resin component, at least a portion of which is a compound (I) having at least one linkage selected from oxiranes, thiiranes, and combinations thereof, substituted on at least three of the substitutable positions on the oxirane and/or thiirane carbons, respectively, with an alkyl, alkenyl or aryl substituent having a carbon content of 1 to about twelve carbon atoms, with or without substitution or interruption by one or more heteroatoms or halogens, as appropriate, provided that the compound I does not include as its sole component an epoxy compound within formula II:

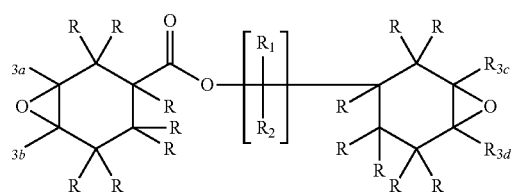

II wherein each R is independently selected from the group consisting of hydrogen, methyl, ethyl, propyl, isopropyl, butyl, isobutyl, tert-butyl, $C_{1-4}$ alkoxy, halogen, cyano and nitro, $R_1$ and $R_2$ are each independently selected from the group consisting of hydrogen, methyl, ethyl, and propyl, provided that both $R_1$ and $R_2$ cannot be hydrogen, and $R_3$ is independently selected from propyl, and isopropyl, provided at least one of $R_{3a}$ and $R_{3b}$, and at least one of $R_{3c}$ and $R_{3d}$ is independently selected from the group consisting of methyl, ethyl, propyl, and isopropyl, and m is 0 or 1. and (b) a curing agent component selected from anhydride compounds, amine compounds, amide compounds, imidazole compounds, and combinations thereof.

Reaction products of these compositions are capable of softening under exposure to elevated temperature conditions, such as in excess of the temperature chosen to cure the composition. Loss of adhesion to the substrate occurs at temperatures greater than that which was used to cure the composition. For instance, at least about 50% of adhesion to the substrate is typically lost at temperatures in excess of about 200° C.

Typically, the composition includes about 10 to about 70 weight percent of the curable resin component, such as about 15 to about 60 weight percent, desirably about 30 to about 50 weight percent, based on the weight of the total composition, of which about 25 to about 75 weight percent, such as about 35 to about 65 weight percent, desirably about 45 to about 55 weight percent, is comprised of a compound having at least one linkage selected from oxiranes, thiiranes, and combinations thereof, substituted on at least three of the substitutable positions on the oxirane and/or thiirane carbons, respectively, with an alkyl, alkenyl or aryl substituent having a carbon content of 1 to about twelve carbon atoms, with or without substitution or interruption by one or more heteroatoms or halogens; and 1 to about 100 weight percent of the curing agent component, based on the total weight of the curable resin component, depending of course on the type and identity of the curing agent chosen.

Of course, depending on the particular set of properties desirable for a composition destined for a specific purpose these values may vary somewhat. Such variation may be achieved without undue experimentation by those persons skilled in the art, and accordingly are contemplated within the scope of the present invention.

The curable resin component of the present invention may include any common epoxy resin, such as a multifunctional epoxy resin. Ordinarily, the multifunctional epoxy resin should be included in an amount within the range of about 10 weight percent to about 80 weight percent, such as about 15 to about 75 weight percent, desirably about 25 to about 60 weight percent, of the total of the epoxy resin component. In the case of bisphenol-F-type epoxy resin, desirably the amount thereof should be in the range of from about 15 to about 60 weight percent, such as about 30 to about 50 weight percent, based on the weight of the curable resin component.

Examples of the multifunctional epoxy resin include bisphenol-A-type epoxy resin, bisphenol-F-type epoxy resin (diglycidyl ether of bisphenol-F-type epoxy resin, such as RE-404-S from Nippon Kayaku, Japan), phenol novolac-type epoxy resin, and cresol novolac-type epoxy from resin (such as "ARALDITE" ECN 1871 from Ciba Specialty Chemicals, Hawthorne, N.Y.).

Other suitable epoxy resins include polyepoxy compounds based on aromatic amines and epichlorohydrin, such as N,N,N',N'-tetraglycidyl-4,4'-diaminodiphenyl methane; N-diglycidyl-4-aminophenyl glycidyl ether; and N,N,N',N'-tetraglycidyl-1,3-propylene bis-4-aminobenzoate.

Among the epoxy resins suitable for use herein also include polyglycidyl derivatives of phenolic compounds, such as those available commercially under the tradename "EPON", such as "EPON" 828, "EPON" 1001, "EPON"

1009, and "EPON" 1031 from Shell Chemical Co.; "DER" 331, "DER" 332, "DER" 334, and "DER" 542 from Dow Chemical Co.; and "BREN-S" from Nippon Kayaku. Other suitable epoxy resins include polyepoxides prepared from polyols and the like and polyglycidyl derivatives of phenol-formaldehyde novolacs, the latter of which are available commercially under the tradename "DEN", such as "DEN" 431, "DEN" 438, and "DEN" 439 from Dow Chemical. Cresol analogs are also available commercially under the tradename "ARALDITE", such as "ARALDITE" ECN 1235, "ARALDITE" ECN 1273, and "ARALDITE" ECN 1299 from Ciba Specialty Chemicals. SU-8 is a bisphenol-A-type epoxy novolac available from Interez, Inc. Polyglycidyl adducts of amines, aminoalcohols and polycarboxylic acids are also useful in this invention, commercially available resins of which include "GLYAMINE" 135, "GLYAMINE" 125, and "GLYAMINE" 115 from F.I.C. Corporation; "ARALDITE" MY-720, "ARALDITE" 0500, and "ARALDITE" 0510 from Ciba Specialty Chemicals and PGA-X and PGA-C from the Sherwin-Williams Co.

Still other epoxy resins that are suitable for use herein include aliphatic epoxies with alkylene oxide residues, examples of which include, but are not limited to, mono-, di- or multi-functional epoxies containing ether linkages, such as primary, secondary and tertary alkylene diol diglycidyl ethers, and epoxies containing mono- or poly-alkylene oxide residues (such as ethylene oxide, propylene oxide, butylene oxide, pentylene oxide, and hexylene oxide residues).

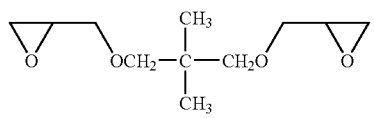

For instance,

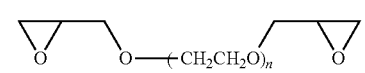

-continued

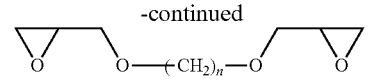

where n is an integer from 1 to about 18, are each appropriate, individually or in combination, for use as at

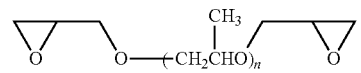

least a portion of the epoxy resin component.

Examples of cycloaliphatic epoxies with alkylene oxide residues include mono-, di- or multi functional cyclohexyl epoxies; hydrated bisphenol A-type epoxies; and hydrated bisphenol F-type epoxies, containing alkylene ether residues. DME-100 (1,4-cyclohexane dimethanol diglycidyl ether, available commercially from New Japan Chemical Co., Ltd.) as shown below is one such example.

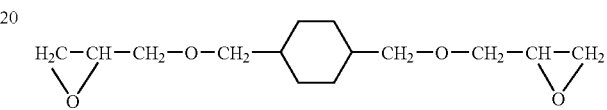

Examples of aromatic epoxies with alkylene oxide residues include mono-, di- or multi-functional epoxies such as bisphenol A type epoxies; bisphenol F type epoxies; phenol novolac type epoxies; and cresol novolac type epoxies, containing alkylene ether residues.

Examples of such epoxies include BEO-60E

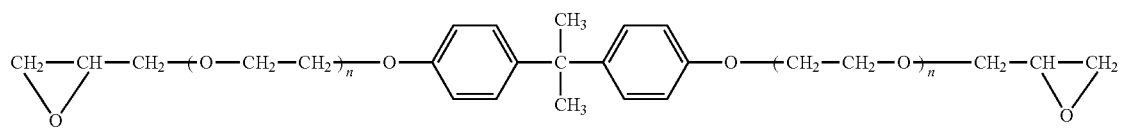

(ethoxylated bisphenol A di-glycidyl ether, available commercially from New Japan Chemical Co., Ltd.), and BPO-20E (propyloxylated bisphenol A di-glycidyl ether, available commercially from New Japan Chemical Co., Ltd.), which are shown below:
where n is an integer between and about 1 and 20, which for BPO-60E n is 1, and

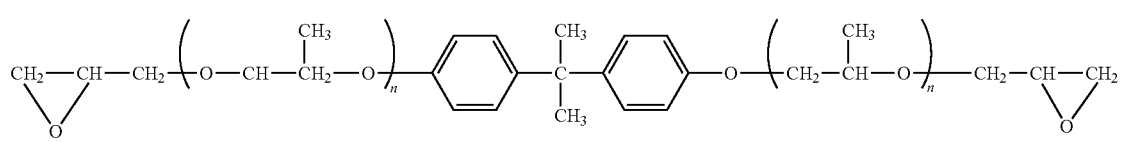

where n is an integer between and about 1 and 20, which for BEO-60E n is 3.

And of course combinations of the different epoxy resins are also desirable for use herein.

The inventive composition, which after cure lends itself to being "reworked" under appropriate conditions, includes a compound having at least one oxirane or thiirane linkage substituted on at least three of the substitutable positions on the oxirane or thiirane carbons, respectfully, with an alkyl, alkenyl or aryl substituent having a carbon content of 1 to about twelve carbon atoms, with or without substitution or interruption by one or more heteroatoms or halogens. When reacted with a curing agent it is believed that these oxirane or thiirane compounds form a tertiary ester (when the curing agent is anhydride based) or a tertiary ether (when the curing agent is nitrogen-based, such as with an imidazole), which linkage is susceptible to controlled degradation under appropriate conditions, such as elevated temperature and/or acidic environment.

Particular examples of such compounds include di- or poly-oxirane and thiirane compounds prepared from 2,10-dimethyl-6-methylene-4,8-bis(2-methyl-1-propenyl-2,4,7, 9-undecatetraene (CAS Reg. No. 249664-51-7), 4-[(4E or 4Z)-1,5-dimethyl-4-heptenylidene or octenylidene]-1-methyl-cyclohexene (CAS Reg. Nos. 221269-56-3, 221269-55-2, 209462-40-8, 209462-39-5), 1,1'-[(1E or 1Z, 3E or 3Z)-5-(1,1-dimethyl-2-propenyl)-3-(3-methyl-2-butenyl)-1,3-pentadiene-1,5-diyl]bis-benzene (CAS Reg. No. 207513-40-4), 4,6-dimethyl-[S or R-(E or Z, Z or E)]-2,5-octadiene (CAS Reg. No. 203515-58-6, 203515-52-0), 2,6,10,14-tetramethyl-7-(3-methyl-4-pentenyl)-2,5,9,13-pentadecatetraene (CAS Reg. No. 202134-68-7), 7-ethyl-3,11-dimethyl-(3Z or 3E, 6E or 6Z, 10Z or 10E)-1,3,6,10-tridecatetraene (CAS Reg. No. 189387-61-9), 3,4,8-trimethyl-1,4,7-nonatriene (CAS Reg. No. 179981-39-6), 13-ethyl-9-methyl-1,9,12-pentadecatetraene (CAS Reg. No. 174189-19-6), 1-methyl-4-(2-methyl-6-heptenylidene)-cyclohexene (CAS Reg. No. 170274-84-7), 2,6,11-trimethyl-(E or Z)-2,5,10-dodecatriene (CAS Reg. No. 169524-63-4), 2,6-dimethyl-(E or Z, E or Z)-2,6,9-tetradecatriene (CAS Reg. No. 169265-90-1), 7-(3-methyl-2-butenyl-(E or Z)-6-dodecene (CAS Reg. No. 168141-30-8), 6-(3-methyl-2-butenyl)-(E or Z)-6-dodecene (CAS Reg. No. 168141-25-1), 2,4,6,6,8-pentamethyl-2,4,7-nonatriene (CAS Reg. No. 164993-09-9), 3,7-dimethyl-1-(methyl)-(E or Z, E or Z)-1,3,6,10-dodecatetraene (CAS Reg. No. 162189-16-4), 5-[3-methyl-1-(2-methyl-1-propenyl)-2-butenylidene]-1,3-cyclopentadiene (CAS Reg. No. 162143-83-1), 4-[(4E or 4Z)-1,5-dimethyl-4-heptenylidene]-1-methyl-(4Z or 4E)-cyclohexene (CAS Reg. No. 160359-81-9), 3,7,11-trimethyl-1,3,6,10-docosatetraene (CAS Reg. No. 159085-88-8), 3,7,11,15-tetramethyl-1,3,6,10-hexadecatetraene (CAS Reg. No. 158729-00-1), 9-ethyl-2,6-dimethyl-(E or Z, E or Z)-2,6,9-dodecatriene (CAS Reg. No. 157337-30-9), 2-methyl-5-propyl-(E or Z)-2,5-nonadiene (CAS Reg. No. 157337-25-2), 3,7,11-trimethyl-(Z or E, E or Z, E or Z)-1,3,6,10-dodecatetraene (CAS Reg. Nos. 154579-52-9, 154579-50-7, 154579-49-4, 154579-40-5), 4,8,12-trimethyl-(Z or E, E or Z, E)-2,4,7,11-tridecatetraene (CAS Reg. Nos. 154579-51-8, 154579-47-2), 1-methyl-4-(2-methyl-6-heptenylidene)-(E or Z)-cyclohexene (CAS Reg. No. 152252-96-5), 3-ethyl-7,11-dimethyl-(E or Z, E or Z)-1,3,6, 10-dodecatetraene (CAS Reg. No. 152195-83-0), 2,6,6,9-tetramethyl-7-(2-methyl-1-propenyl)-2,4,8-decatriene (CAS Reg. No. 150280-97-0), 2,7-dimethyl-4,5-bis(2-methyl-1-propenyl)-2,6-octadiene (CAS Reg. No. 150280-96-9), 3,7-dimethyl-1,3,6-octatriene (CAS Reg. No. 147727-60-4), 2-methyl-5-(1-methylethylidene)-cyclohexene (CAS Reg. No. 147727-51-3), 2,6-dimethyl-5-(1-methylethylidene)-1, 3-cyclohexadiene (CAS Reg. No. 138434-36-3), 2,6-dimethyl-2,57 decadiene or octadiene (CAS Regs. Nos. 134956-14-2, 128144-73-0), 7-ethyl-3,11-dimethyl-1,3,6,10-dodecatetraene (CAS Reg. No. 134779-29-6), 2-methyl-(E or Z)-2,5-octadiene (CAS Reg. No. 133797-14-5), 7-ethyl-3, 11-dimethyl-(E or Z, E or Z)-1,3,6,10-dodecatetraene (CAS Reg. No. 127941-96-2), 2,7,11-trimethyl-(E or Z)-2,5,10-dodecatriene (CAS Reg. No. 124745-43-3), 6,10-dimethyl-(Z or E, Z or E)-2,6,9-undecatrien-4-yne (CAS Reg. No. 122305-03-7), 2,6-dimethyl-(Z or E)-2,5-dodecadiene (CAS Reg. No. 121403-30-3), 2,7-dimethyl-4,5-bis(2-methyl-1-propenyl)-2,4,6-octatriene (CAS Reg. No. 117712-68-2), 2,3,6,7-tetramethyl-1,3,6-octatriene (CAS Reg. No. 117527-68-1), 2-methyl-5-propyl-(Z or E)-2,5-dodecadiene (CAS Reg. No. 116893-95-9), 2-methyl-5-(1-methylethyl)-(E or Z)-2,5-dodecadiene (CAS Reg. No. 116893-93-7), 2-methyl-(Z or E)-2,5-dodecadiene (CAS Reg. No. 116893-92-6), 2,4,4-trimethyl-(E or Z)-2,5-heptadiene (CAS Reg. No. 116786-15-3), 2,6-dimethyl-2,5-octadiene (CAS Reg. No. 116668-48-5), 3,4,7,11-tetramethyl- (E or Z, Z or E)-1,3,6,10-dodecatriene (CAS Reg. Nos. 114091-33-7, 114091-32-6), 3,7,11-trimethyl-(E or Z, E or Z)-1,3,6,10-dodecatetraene (CAS Reg. No. 113244-64-7), 4,8-dimethyl-1,4,7-nonatriene (CAS Reg. No. 110559-67-6), 3,7,11,15-tetramethyl-1,3,6,10,14-hexadecapentaene (CAS Reg. No. 110249-03-1), 2-methyl-(Z or E)-2,5-pentadecadiene (CAS Reg. Nos. 108181-16-4, 108181-15-3), 2-methyl-5-(1-methylethylidene)-2-decene (CAS Reg. No. 107909-37-5), 2,6-dimethyl-2,5,7-decatriene (CAS Reg. No. 105694-90-4), 4,8-dimethyl-2,4,7-nonatriene (CAS Reg. No. 105694-88-0), 15,19,23-trimethyl-15,18,22-heptatriacontatriene (CAS Reg. No. 104519-12-2), 8-(2-methyl-1-propenyl)-6-tetradecene (CAS Reg. No. 10229-83-2), 3,7,11-trimethyl-(E or Z)-1,3,6,10-dodecatetraene (CAS Reg. No. 97885-54-6), 3,4-didehydro-2-(3-methyl-2-butenyl)-carotene (CAS Reg. No. 97231-43-1), 7-ethyl-3,11-dimethyl-1,3,6,10-dodecatetraene (CAS Reg. No. 96890-21-0), 1,3-dimethyl-4-propylidene-cyclopentene (CAS Reg. No. 96095-54-4), 2,7,11-trimethyl-(E or Z, E or Z)-1,3,6,10-dodecatetraene (CAS Reg. No. 93517-88-5), 6,10-dimethyl-1,4,6,9-undecatetraene (CAS Reg. No. 93308-70-4), 2-(1-methylethyl)-5-(1-methylethylidene)-1,3-cyclohexadiene (CAS Reg. No. 92545-19-2), 2-ethyl-5-ethylidene-cyclohexadiene (CAS Reg. No. 92545-18-1), 2-methyl-5-(1-methylethylidene)-1,3-cyclohexadiene (CAS Reg. No. 92545-16-9), 3,7,10-trimethyl-(Z or E, E or Z)-1,3,6-undecatriene (CAS Reg. No. 91203-72-4), 4-(1,5-dimethyl-4-hexenylidene)-1-methyl-cyclohexene (CAS Reg. No. 90458-95-0), 1-methyl-4-(1-methylethylidene)-cyclohexene (CAS Reg. No. 83259-95-4), 2,5-dimethyl-(Z or E)-2,5-heptadiene (CAS Reg. Nos. 83180-40-9, 83180-39-6), 2-methyl-5-(1-methylethylidene)-1,3-cyclohexadiene (CAS Reg. No. 81719-66-6), 2,6,10-trimethyl-(E or Z, Z or E)-2,6,9-tetradecatriene (CAS Reg. No. 80873-82-1), 6-methyl-(Z or E, E or Z)-2,5-dodecadiene (CAS Reg. Nos. 80873-79-6, 80873-78-5), 2,3,6-trimethyl-(E or Z, E or Z)-1,3,6-octatriene (CAS Reg. No. 80651-22-5), tetrahydro-3,7,11-trimethyl-1,3,6,10-dodecatetraene (CAS Reg. No. 80338-47-2), 3,4,7,11-tetramethyl-1,3,6,10-dodecatetraene (CAS Reg. No. 7983-34-9), 3,4,7,11-tetramethyl-(Z or E, Z or E)-1,3,6,10-dodecatetraene (CAS Reg. No. 79383-33-8), 2,6-dimethyl-4-methylene-2,5-heptadiene (CAS Reg. No. 77832-43-6), 5-ethyl-2-methyl-2,5-heptadiene (CAS Reg. No. 78811-91-3), 2,5-dimethyl-2,5-heptadiene or octadiene (CAS Reg. Nos. 78811-90-2, 78811-89-9), 3,7,11-trimethyl-dodecatriene (CAS Reg. No. 78339-48-7), 2,4,6,6,8-pentamethyl-(E or Z)-2,4,7-nonatriene (CAS Reg. No. 78310-14-2), 3,7-diethyl-1-methyl-1,3,6,10-tridecatetraene (CAS Reg. No. 78216-57-6), 7-ethyl-3,11-dimethyl-1,3,6,10-tridecatetraene (CAS Reg. No. 78183-46-7), 2,6-dimethyl-(E or Z)-2, 5-dodecadiene (CAS Reg. No. 77958-38-4), 2,6,10-trimethyl-(E or Z, E or Z)-2,6,9-tetradecatriene (CAS Reg. No. 77958-36-2), 3,7,11,15-tetramethyl-(Z or E, E or Z, E or Z)-1,3,6,10,14-hexadecapentaene (CAS Reg. No. 77898-98-

7), 3,7,11,15-tetramethyl-(3E or 3Z, 6E or 6Z, 10E or 10Z)-1,3,6,10,14-hexadecapentaene (CAS Reg. No. 77898-97-6), 1-ethenyl-4-(1-methylethylidene)-cyclohexene (CAS Reg. No. 77142-28-0), 1-methyl-6-methylene-4-(1-methylethylidene)-cyclohexene (CAS Reg. No. 77142-23-5), 3,7,11-trimethyl-1,3,6-dodecatriene (CAS Reg. No. 74253-06-8), 4-(1,5-dimethylhexylidene)-1-methyl-cyclohexene (CAS Reg. No. 74253-05-7), 7-ethyl-3,11-dimethyl-(3Z or 3E, 6E or 6Z)-1,3,6,10-dodecatetraene (CAS Reg. No. 73690-00-3), 1,3,3',4,4',16-hexadehydro-1,2-dihydro-2,2'-bis(3-carotene (CAS Reg. No. 77365-74-9), 7-methyl-(Z or E, Z or E)-3,6-dodecadiene (CAS Reg. Nos. 72858-64-1, 72858-63-0), 6-ethylidene-2,3,10-trimethyl-(E or Z, E or Z)-1,3,9-undecatriene (CAS Reg. No. 72564-39-7), 2,3,6,7,10,11-hexamethyl-(E or Z, E or Z)-1,3,6,10-dodecatetraene (CAS Reg. No. 72564-36-4), 2,3,6,7-tetramethyl-(E or Z)-1,3,6-octatriene (CAS Reg. No. 72564-35-3), 2,7,11-trimethyl-1,3,6,11-dodecatetraene (CAS Reg. No. 71803-35-5), 3,7,11,15,19,23,27,31,35-nonamethyl-1,3,6,10,14,18,22,26,30,34-hexatriacontadecaene (CAS Reg. No. 71278-21-2), 2,6-dimethyl-9-propyl-2,6,9-tridecatriene (CAS Reg. No. 70602-78-7), 3,6-dimethyl-(E or Z, E or Z)-1,3,6-octatriene (CAS Reg. No. 70569-76-5), 3,7-diethyl-11-methyl-(3Z or 3E, 6E or 6Z) 1,3,6,10-tridecatetraene (CAS Reg. No. 70239-70-2), 7-ethyl-3,11-dimethyl-(3Z or 3E, 6E or 6Z)-1,3,6,10-tridecatetraene (CAS Reg. No. 70234-77-4), 1-methyl-4-(5-methyl-4-hexenylidene)-(4E or 4Z)-cyclohexene (CAS Reg. No. 66916-06-9), 2,6,10-trimethyl-(Z or E)-2,5,9-undecatriene (CAS Reg. Nos. 68974-97-0, 68974-96-9), 2,6,7,7-tetramethyl-(Z or E)-2,5-octadiene (CAS Reg. Nos. 68974-95-8, 68974-94-7), 2,6,10,11,11-pentamethyl-2,6,9-dodecatriene (CAS Reg. No. 68965-68-4), 2,6,10-trimethyl-2,6,9-tetradecatriene (CAS Reg. No. 68965-67-3), 2,6-dimethyl-(Z or E)-2,5-decadiene (CAS Reg. Nos. 68965-66-2, 68965-65-1), 6,10-dimethyl-1,6,9-undecatrien-4-yne (CAS Reg. No. 68483-39-6), 2,3,6-trimethyl-2,5-heptadiene (CAS Reg. No. 67796-57-0), 2,4-dimethyl-(E or Z)-2,5-heptadiene (CAS Reg. No. 67796-55-8), 2,7,11-trimethyl-(E or Z, E or Z)-1,3,6,11-dodecatetraene (CAS Reg. No. 67023-83-0), 6-ethyl-3-methyl-2,5-decadiene (CAS Reg. No. 65668-94-2), 2,6,10-trimethyl-(Z or E)-2,5-undecadiene (CAS Reg. Nos. 64583-07-9, 64583-04-6), 3,7-dimethyl-3,6-octadien-1-yne (CAS Reg. No. 64547-65-5), 2,7,10-trimethyl-1,6,9-undecatriene (CAS Reg. No. 61058-91-1), 4,5-dimethyl-(E or Z, E or Z, E or Z)-3,5,8-undecatriene (CAS Reg. No. 59681-86-6), 4,5-dimethyl-2,5,8-undecatriene (CAS Reg. No. 59681-84-4), 1'-[4-methyl-2-(2-methyl-1-propenyl)-1,3-pentadienylidene]bis-benzene, 1 (CAS Reg. No. 55861-06-8), 4-(1,5-dimethyl-4-hexenylidene)-1-methyl-(4E or 4Z)-cyclohexene (CAS Reg. No. 53585-13-0), 2,6,11,15-tetramethyl-(Z or E)-2,6,9,14-hexadecatetraene (CAS Reg. Nos. 53254-62-9, 53254-61-8), [3-methyl-1-(2-methyl-1-propenyl)-2-butenyl]-benzene (CAS Reg. No. 53210-24-5), 2,6,11-trimethyl-(E or Z, E or Z)-2,6,9-dodecatriene (CAS Reg. No. 51795-79-0), 2,6-dimethyl-(E or Z, E or Z)-2,6,9-dodecatriene (CAS Reg. No. 51795-74-5), 2,3,6,7,10,11-hexamethyl-1,3,6,11-dodecatetraene (CAS Reg. No. 45214-38-8), 19-methyl-1-(2-methyl-1-2,4,6,8,10,12,14,16,18-eicosanonaenylium (CAS Reg. No. 40544-26-1), 17-methyl-1-(2-methyl-1-propenyl)-2,4,6,8,10,12,14,16-octadecaoctaenylium (CAS Reg. No. 40544-25-0), 15-methyl-1-(2-methyl-1-propenyl)-2,4,6,8,10,12,14-hexadecaheptaenylium (CAS Reg. No. 40544-24-9), 13-methyl-1-(2-methyl-1-propenyl)-2,4,6,8,10,12-tetradecahexaenylium (CAS Reg. No. 40544-23-8), 11-methyl-1-(2-methyl-1-propenyl)-2,4,6,8,10-dodecapentaenylium (CAS Reg. No. 40544-22-7), 9-methyl-1-(2-methyl-1-propenyl)-2,4,6,8-decatetraenylium (CAS Reg. No. 40544-21-6), 7-methyl-1-(2-methyl-1-propenyl)-2,4,6-octatrienylium (CAS Reg. No. 40544-20-5), 4,ethylidene-2,6-dimethyl-2,5-heptadiene (CAS Reg. No. 39117-23-2), 3,7,11-trimethyl-(E or Z)-3,6,11-dodecatrien-1-yne (CAS Reg. No. 36629-58-0), 3,7-dimethyl-(3E or 3Z)-3,6-octadien-1-yne (CAS Reg. Nos. 36602-32-1, 36602-31-0), 3,7-dimethyl-(E or Z)-3,6-nonadien-1-yne (CAS Reg. Nos. 36597-67-8, 36597-66-7), 3,6,7-trimethyl-(E or Z)-3,6-octadien-1-yne (CAS Reg. Nos. 36597-64-5, 36957-63-4), 7-ethyl-3-methyl-(E or Z)-3,6-nonadien-1-yne (CAS Reg. Nos. 36597-61-2, 36597-60-1), 3,7,11-trimethyl-(Z or E)-3,6,11-dodecatrien-1-yne (CAS Reg. Nos. 36597-58-7, 36597-56-5, 36597-56-4), 2,3,6,7,10,11-hexamethyl-1,3,6,11-dodecatetraene (CAS Reg. No. 34888-55-6), 2,6-dimethyl-2,5-heptadiene (CAS Reg. No. 34484-31-6), 2-methyl-2,5-heptadiene (CAS Reg. No. 34484-29-2), 3,6,10-trimethyl-2,5,7,10-dodecatetraene (CAS Reg. No. 32945-35-0), 2,7,10-trimethyl-1,3,7,10-dodecatetraene (CAS Reg. No. 32925-31-8), 3,6-dimethyl-1,3,6-octatriene (CAS Reg. No. 32778, 725-9), 12-(2,2-dimethyl-6-methylenecyclohexyl)-3,8,8-trimethyl-11-methylene-(E or Z)-(S)-1,3,6-dodecatriene (CAS Reg. No. 29738-44-1), ocimene (CAS Reg. No. 29223-32-3), 3,7,11-trimethyl-, (3Z or 3E, 6Z or 6E)-1,3,6,10-dodecatetraene (CAS Reg. Nos. 28973-99-1, 28973-98-0, 26560-14-5), 2-methyl-4-methylene-2,5-heptadiene (CAS Reg. No. 24498-9-5), 3,8,8,14,18-pentamethyl-11-methylene-(E or Z)-1,3,6,13,17-nonadecapentaene (CAS Reg. No. 23192-59-8), 2,7-dimethyl-2,5-octadiene (CAS Reg. No. 20733-73-7), 3,8,8,14,18-pentamethyl-11-methylene-(E or Z, E or Z, E or Z)-1,3,6,13,17-nonadecapentaene (CAS Reg. No. 19953-95-8), 6,10-dimethyl-2,4,6,9-undecatetraene (CAS Reg. No. 19048-50-1), 2-methyl-(Z or E)-2,5-heptadiene (CAS Reg. No. 18316-09-1), 2-methyl-(E or Z)-2,5-heptadiene (CAS Reg. No. 18316-08-0), 3,7-dimethyl-1,3,6-octatriene (CAS Reg. No. 13877-91-3), 4-(1,5-dimethyl-4-hexenylidene)-1-methyl-(4Z or 4E)-cyclohexene (CAS Reg. No. 13062-00-5), 2,6,10,14,19,22,27,31-octamethyl-2,6,10,14,16,18,22,26,30-dotriacontanonaene (CAS Reg. No. 13050-81-2), 2,6-dimethyl-2,5-heptadiene (CAS Reg. No. 6090-16-0), 4-(1,5-dimethyl-4-hexenylidene)-1-methyl-cyclohexene (CAS Reg. No. 5957-36-8), 3,7-dimethyl-(3E or 3Z)-1,3,6-octatriene (CAS Reg. No. 3779-61-1), 2,6,10,14,19,23,31-heptamethyl-2,5,10,14,16,18,22,26,29-dotriacontanonaene (CAS Reg. No. 3625-51-2), 3,7,dimethyl-(3Z or 3E)-1,3,6-octatriene (CAS Reg. No. 3338-55-4), 3-methyl-1-(2-methyl-1-propenyl)-(E or Z)-2-pentenyl (CAS Reg. No. 3229-66-1), 2,6-dimethyl-4-(2-methylpropenyl)-1,3,5-heptatriene (CAS Reg. No. 1606-44-6), 2,6-dimethyl-4-methylene-2,5-heptadiene (CAS Reg. No. 927-02-6), 1-methyl-4-(1-methylethylidene)-cyclohexene (CAS Reg. No. 586-62-9), 3,7,11-trimethyl-(3E or 3Z, 6E or 6Z)-1,3,6,10-dodecatetraene (CAS Reg. No. 502-61-4), 4-(1,5-dimethyl-4-hexenylidene)-1-methyl-cyclohexene (CAS Reg. No. 495-62-5), isoprene, myrcene, dihydromyrene, linalool, terpinenes (α, β, and ᛞ), limonene, terpinolene, menthadiene (p-3,8 or p-2,4), geraniol, nerol, geranylacetate, neryl acetate, nerolidol (CAS Reg. No. 7212-44-4), farnesol (CAS Reg. No. 4602-14-0), dehydronerolidol (CAS Reg. No. 2387-68-0), ↦-bisabolol, valancene, nookatene, nootkatone, dimethyl-2,4,6-octatriene, ᛞ-phellandrences (CAS Reg. No. 6153-17-9), piperitols (−, cis and +, trans) (CAS Reg. Nos. 65733-28-0, 65733-2-9), 1-methyl-1,4-cyclohexadiene, methyl cyclopentadiene dimer, ethylidene norbornene, dipentene, carvestrene, carvone (− or +), alloocimenes [4-trans-6-cis (CAS Reg. No. 7216-56-0) and 4-trans-6-trans (CAS Reg. No. 3016-19-1)], alloocimenols (CAS Reg. No. 18479-54-4), ionomers (CAS Reg. Nos. 127-41-3, 14901-07-6), guaiazulene, lanosterol (CAS Reg. No. 76-63-0), squalene (CAS Reg. No. 111-02-4), lycopene (CAS Reg. No. 502-65-8), and carotenes [↕ and ⇕(CAS Reg. Nos. 7235-40-7, 472-94-5)].

Of course, combinations of these compounds, with or without conventional epoxy compounds, may be used, provided that excluded as the sole component from these compounds are those within the teachings of U.S. Pat. Nos. 5,948,922 (Ober) and 5,973,033 (Ober). That is, excluded as the sole component from these compounds are epoxy compounds within the following formula:

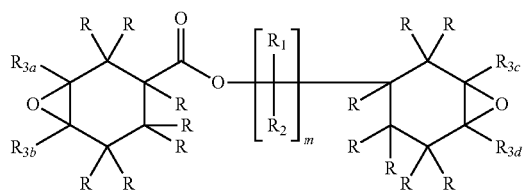

where each R is independently selected from hydrogen, methyl, ethyl, propyl, isopropyl, butyl, isobutyl, tert-butyl, $C_{1-4}$ alkoxy, halogen, cyano and nitro, $R_1$ and $R_2$ are each independently selected from hydrogen, methyl, ethyl and propyl, provided that both $R_1$ and $R_2$ cannot be hydrogen, $R_3$ is independently selected from hydrogen, methyl, ethyl, propyl, and isopropyl, provided at least one of $R_{3a}$ and $R_{3b}$, and at least one of $R_{3c}$ and $R_{3d}$ is independently selected from methyl, ethyl, propyl, and isopropyl, and m is 0 or 1.

Particularly desirable epoxy or oxirane compounds within formula I include limonene diepoxide and gamma-terpinene diepoxide. Limonene diepoxide may be obtained commercially from Daicel Chem. Co., Ltd., Japan under the tradename "CELLOXIDE" 3000.

Other particularly desirable epoxy or oxirane compounds include methyl cyclopentadiene diepoxide dimer ("MCPD dimer"), ethylidene norbornene diepoxide ("ENB diepoxide"), and nopol epoxide glycidyl ether ("NEGE").

The presence in the curable resin component of one or more epoxy compounds having at least one oxirane or thiirane linkage substituted on at least three of the substitutable positions on the oxirane or thiirane carbons, respectfully, with an alkyl, alkenyl or aryl substituent having a carbon content of one to about twelve carbon atoms, with or without substitution or interruption by one or more heteroatoms or halogens allows for repair, replacement, recovery and/or recycling of operative electronic components from assemblies that have become at least in part inoperative.

The compounds with the oxirane linkage(s) can be prepared from olefinically unsaturated compounds, many of which having at least two olefinic linkages, with at least one of the olefinic linkages being substituted on at least three of the substitutable positions on the epoxy carbons with an alkyl, alkenyl or aryl substituent having a carbon content of 1 to about twelve carbon atoms, with or without substitution or interruption by one or more heteroatoms or halogens. This olefinically unsaturated compound may then be contacted with an epoxidation agent in an amount and under conditions appropriate to react with the olefinic linkages to form an inventive compound having an oxirane linkage.

Appropriate epoxidation agents useful in forming oxirane rings include peracids (such as peracetic acid, perbenzoic acid, meta-chloroperbenzoic acid, tungstic acid/hydrogen peroxide [see U.S. Pat. Nos. 4,562,276 (Venturello) and 5,274,140 (Venturello) and the like], with the reaction carried out until epoxidization of the olefin linkages is at least substantially complete, typically within a period of time of from 2 to 18 hours.

As regards preparation of inventive compounds having at least one thiirane linkage, conventional synthetic methods may be used, such as those described in U.S. Pat. No. 3,378,522 (Martin), the disclosure of which is hereby expressly incorporated herein by reference.

To that end, particularly desirable episulfide or thiirane compounds within formula I include the episulfides or thiiranes of limonene, gamma-terpinene, methyl cyclopentadiene dimer, ethylidene norbornene, and nopol glycidyl ether.

As an inorganic filler component, many materials are potentially useful. For instance, the inorganic filler component may often include reinforcing silicas, such as fused silicas, and may be untreated or treated so as to alter the chemical nature of their surface. Virtually any reinforcing fused silica may be used.

Particularly desirable ones have a low ion concentration and are relatively small in particle size (e.g., in the range of about 2-10 microns, such as on the order of about 2 microns), such as the silica commercially available from Admatechs, Japan under the trade designation S0-E5.

Other desirable materials for use as the inorganic filler component include those constructed of or containing aluminum oxide, silicon nitride, aluminum nitride, silica-coated aluminum nitride, boron nitride and combinations thereof.

The inorganic filler component may be present in the inventive composition in an amount up to 70 weight percent, such as in the range of about 5 to about 60 weight percent, particularly about 10 to about 50 weight percent, more particularly about 15 to about 40 weight percent, and even more particularly about 20 to about 35 weight percent, such as about 30 weight percent.

The curing agent component should include materials capable of catalyzing the polymerization of the epoxy resin component of the inventive compositions. Desirable curing agents for use with the present invention include an anhydride component, a nitrogen-containing component, such as an amine compound, an amide compound, and an imidazole compound, or combinations thereof.

Appropriate anhydride compounds for use herein include mono- and poly-anhydrides, such as hexahydrophthalic anhydride ("HHPA") and methyl hexahydrophthalic anhydride ("MHHPA") (commercially available from Lindau Chemicals, Inc., Columbia, S.C., used individually or as a combination, which combination is available under the trade designation "LINDRIDE" 62C) and 5-(2,5-dioxotetrahydrol)-3-methyl-3-cyclohexene-1,2-dicarboxylic anhydride (commercially available from ChrisKev Co., Leewood, Kans. under the trade designation B-4400).

Of course, combinations of these anhydride compounds are also desirable for use in the compositions of the present invention.

The nitrogen-containing compound includes amine compounds such as polyamines and di- and tri-aza compounds, modified amine compounds, amide compounds, imidazole compounds, and combinations thereof.

Examples of the amine compounds include the following alkyl poly amines: diethylenetriamine, triethylenetetramine, diethylaminopropylamine, and quinoxaline.

Examples of the di- or tri-aza compounds include:

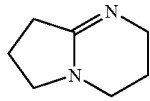

1,5-diazabicyclo[4.3.0]non-5-ene

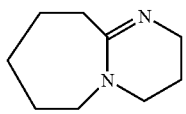

1,8-diazabicyclo[5.4.0]undec-7-ene ("DBU");

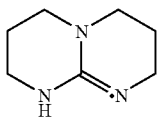

1,5,7-triazabicyclo[4.4.0]dec-5-ene; and
the bicyclo mono- and di-aza compounds:

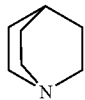

quinuclidine; and

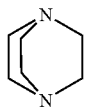

1,4-diazabicyclo[2.2.2.]octane.

Examples of modified amine compounds include epoxy amine additives formed by the addition of an amine compound to an epoxy compound.

Of course, combinations of these amine compounds are also desirable for use in the compositions of the present invention.

Examples of amide compounds include cyano-functionalized amides, such as dicyandiamide.

The imidazole compounds may be chosen from imidazole, isoimidazole, and substituted imidazoles—such as alkyl-substituted imidazoles (e.g., 2-methyl imidazole, 2-ethyl-4-methylimidazole, 2,4-dimethylimidazole, butylimidazole, 2-heptadecenyl-4-methylimidazole, 2-undecenylimidazole, 1-vinyl-2-methylimidazole, 2-n-heptadecylimidazole, 2-undecylimidazole, 2-heptadecylimidazole, 1-benzyl-2-methylimidazole, 1-propyl-2-methylimidazole, 1-cyanoethyl-2-methylimidazole, 1-cyanoethyl-2-ethyl-4-methylimidazole, 1-cyanoethyl-2-undecylimidazole, 1-cyanoethyl-2-phenylimidazole, 1-guanaminoethyl-2-methylimidazole and addition products of an imidazole and trimellitic-acid, 2-n-heptadecyl-4-methylimidazole and the like, generally where each alkyl substituent contains up to about 17 carbon atoms and desirably up to about 6 carbon atoms), and aryl-substituted imidazoles [e.g., phenylimidazole, benzylimidazole, 2-methyl-4,5-diphenylimidazole, 2,3,5-triphenylimidazole, 2-styrylimidazole, 1-(dodecyl benzyl)-2-methylimidazole, 2-(2-hydroxyl-4-t-butylphenyl)-4,5-diphenylimidazole, 2-(2-methoxyphenyl)-4,5-diphenylimidazole, 2-(3-hydroxyphenyl)-4,5-diphenylimidazole, 2-(p-dimethylaminophenyl)-4,5-diphenylimidazole, 2-(2-hydroxyphenyl)-4,5-diphenylimidazole, di(4,5-diphenyl-2-imidazole)-benzene-1,4, 2-naphthyl-4,5-diphenylimidazole, 1-benzyl-2-methylimidazole, 2-p-methoxystyrylimidazole, and the like, generally where each aryl substituent contains up to about 10 carbon atoms and desirably up to about 8 carbon atoms].

Examples of commercial imidazole compounds are available from Air Products, Allentown, Pa. under the trade designation "CUREZOL" 1B2MZ and from Synthron, Inc., Morganton, N.C. under the trade designation "ACTIRON" NXJ-60.

Examples of the modified imidazole compounds include imidazole adducts formed by the addition of an imidazole compound to an epoxy compound. For instance, "AJICURE" PN-23, commercially available from Ajinomoto Co., Inc., Tokyo, Japan, is believed to be an adduct of EPON 828 (bisphenol-A-type epoxy resin, epoxy equivalent 184-194, commercially available from Shell Chemical Co.), 2-ethyl-4-methylimidazole and phthalic anhydride. Others commercially available ones from Ajinomoto include "AMICURE" MY-24, "AMICURE" GG-216 and "AMICURE" ATU CARBAMATE. In addition, "NOVACURE" HX-3722 (an imidazole/bisphenol A epoxy adduct dispersed in bisphenol A epoxy) and "NOVACURE" HX-3921 HP, commercially available from Asahi-Ciba, Ltd., may also be used.

Of course, combinations of these imidazole compounds are also desirable for use in the compositions of the present invention.

The curing agent component may be used in an amount of from about 1 to about 100 weight percent, such as about 3 to about 50 weight percent, based on the weight of the curable resin component, depending of course on the type and identity of the curing agent component.

In addition, the composition may also include a flowability agent, such as a silane and/or titanate.

Appropriate silanes for use herein include octyl trimethoxy silane (commercially available from OSI Specialties Co., Danbury, Conn. under the trade designation A-137), and methacryloxy propyl trimethoxy silane (commercially available from OSI under the trade designation A-174).

Appropriate titanates for use herein include titanium IV tetrakis [2,2-bis[(2-propenyloxy)methyl]-1-butanolato-0] [bis(ditridecylphosphito-0), dihydrogen]$_2$ (commercially available from Kenrich Petrochemical Inc., Bayonne, N.J. under the trade designation KR-55).

When used, the flowability agent may be used in an amount up to about 5 weight percent, such as about 0.05 weight percent to about 2 weight percent, desirably about 0.1 to about 1 weight percent, based on the total weight of the composition.

In addition, adhesion promoters, such as the silanes, glycidyl trimethoxysilane (commercially available from OSI under the trade designation A-187) or gamma-amino propyl triethoxysilane (commercially available from OSI under the trade designation A-1100), may be used.

When used, the adhesion promoters may be used in an amount of about 1 to about 20 weight percent, such as about 5 to about 15 weight percent, desirably about 8 to about 12 weight percent, based on the total weight of the composition.

Cyanate esters may also be used in the inventive compositions. The cyanate esters useful as a component in the inventive compositions may be chosen from dicyanatobenzenes, tricyanatobenzenes, dicyanatonaphthalenes, tricyanatonaphthalenes, dicyanatobiphenyl, bis(cyanatophenyl)methanes and alkyl derivatives thereof, bis(dihalocyanatophenyl)propanes, bis(cyanatophenyl)ethers, bis(cyanatophenyl)sulfides, bis(cyanatophenyl)propanes, tris(cyanatophenyl)phosphites, tris(cyanatophenyl)phosphates, bis(halocyanatophenyl)methanes, cyanated novolac, bis[cyanatophenyl(methylethylidene)]benzene, cyanated bisphenol-terminated thermoplastic oligomers, and combinations thereof.

More specifically, aryl compounds having at least one cyanate ester group on each molecule and may be generally represented by the formula $Ar(OCN)_m$, where Ar is an aromatic radical and m is an integer from 2 to 5. The aromatic radical Ar should contain at least 6 carbon atoms, and may be derived, for example, from aromatic hydrocarbons, such as benzene, biphenyl, naphthalene, anthracene, pyrene or the like. The aromatic radical Ar may also be derived from a polynuclear aromatic hydrocarbon in which at least two aromatic rings are attached to each other through a bridging group. Also included are aromatic radicals derived from novolac-type phenolic resins—i.e., cyanate esters of these phenolic resins. The aromatic radical Ar may also contain further ring-attached, non-reactive substituents.

Examples of such cyanate esters include, for instance, 1,3-dicyanatobenzene; 1,4-dicyanatobenzene; 1,3,5-tricyanatobenzene; 1,3-, 1,4-, 1,6-, 1,8-, 2,6- or 2,7-dicyanatonaphthalene; 1,3,6-tricyanatonaphthalene; 4,4'-dicyanatobiphenyl; bis(4-cyanatophenyl)methane and 3,3',5,5'-tetramethyl bis(4-cyanatophenyl)methane; 2,2-bis(3,5-dichloro-4-cyanatophenyl)propane; 2,2-bis(3,5-dibromo-4-dicyanatophenyl)propane; bis(4-cyanatophenyl)ether; bis(4-cyanatophenyl)sulfide; 2,2-bis(4-cyanatophenyl)propane; tris(4-cyanatophenyl)-phosphite; tris(4-cyanatophenyl) phosphate; bis(3-chloro-4-cyanatophenyl)methane; cyanated novolac; 1,3-bis[4-cyanatophenyl-1-(methylethylidene)]benzene and cyanated bisphenol-terminated polycarbonate or other thermoplastic oligomer.

Other cyanate esters include cyanates disclosed in U.S. Pat. Nos. 4,477,629 and 4,528,366, the disclosure of each of which is hereby expressly incorporated herein by reference; the cyanate esters disclosed in U.K. Pat. No. 1,305,702, and the cyanate esters disclosed in International Patent Publication WO 85/02184, the disclosure of each of which is hereby expressly incorporated herein by reference. Of course, combinations of these cyanate esters within the imidazole component of the compositions of the present invention are also desirably employed herein.

A particularly desirable cyanate ester for use herein is available commercially from Ciba Specialty Chemicals, Tarrytown, N.Y. under the tradename "AROCY" L10 [1,1-di(4-cyanatophenylethane)].

When used, the cyanate esters may be used in an amount of about 1 to about 20 weight percent, such as about 5 to about 15 weight percent, desirably about 8 to about 12 weight percent, based on the total weight of the epoxy resin component.

Conventional additives may also be used in the compositions of the present invention to achieve certain desired physical properties of the composition, the cured reaction product, or both.

For instance, it may be desirable in certain instances (particularly where a large volume of inorganic filler component is used) to include a reactive co-monomer component for the curable resin component, such as a reactive diluent.

Appropriate reactive diluents for use herein may include monofunctional or certain multifunctional epoxy resins and episulfides. The reactive diluent should have a viscosity which is lower than that of the curable resin component. Ordinarily, the reactive diluent should have a viscosity less than about 250 cps. In the event such a monofunctional epoxy resin is included as a reactive diluent, such resin should be employed in an amount of up to about 50 weight percent, based on weight of the curable resin component.

The monofunctional epoxy resin should have an epoxy group with an alkyl group of about 6 to about 28 carbon atoms, examples of which include $C_{6-28}$ alkyl glycidyl ethers, $C_{6-28}$ fatty acid glycidyl esters and $C_{6-28}$ alkylphenol glycidyl ethers.

Commercially available monofunctional epoxy resin reactive diluents include those from Pacific Epoxy Polymers, Richmond, Mich., under the trade designations PEP-6770 (glycidyl ester of neodecandoic acid), PEP-6740 (phenyl glycidyl ether) and PEP-6741 (butyl glycidyl ether).

Commercially available multifunctional epoxy resin reactive diluents include those from Pacific Epoxy Polymers, under the trade designations PEP-6752 (trimethylolpropane triglycidyl ether) and PEP-6760 (diglycidyl aniline).

The compositions of the present invention may, further include other additives, such as defoaming agents, leveling agents, dyes, and pigments. Moreover, photopolymerization initiators may also be incorporated therein, provided that such initiators do not adversely affect the properties of the composition or reaction products formed therefrom.

The present invention also includes novel diepoxide-containing compounds, set forth in detail below.

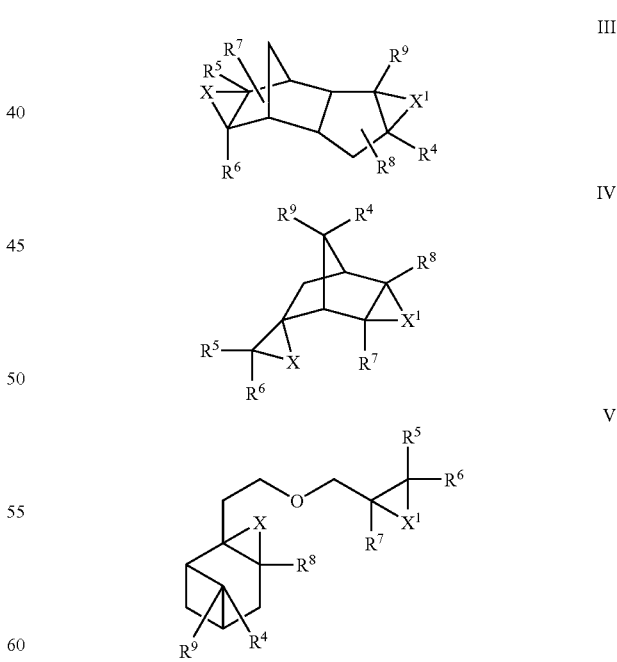

were $R^4$, $R^5$, $R^6$, $R^7$, $R^8$, and $R^9$ are individually selected from the group consisting of hydrogen, alkyl from one to eight carbon atoms, alkenyl from two to eight carbon atoms and combinations thereof, and X and $X^1$ are individually selected from O and S More specific examples of such novel diepoxide-containing compounds include:

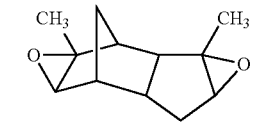
VI

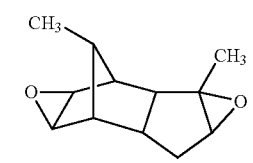
VII

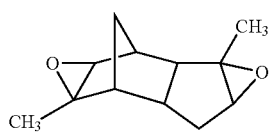
VIII

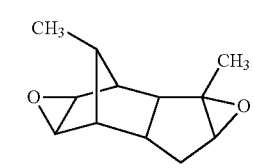
IX

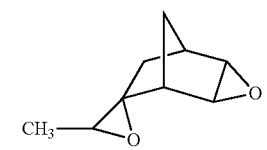
X

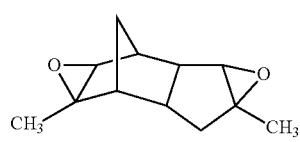
XI

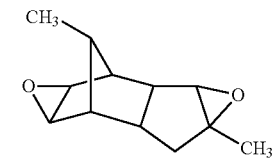
XII

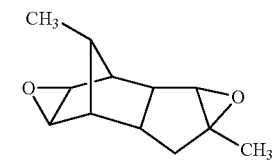
XIII

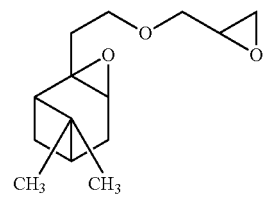
XIV

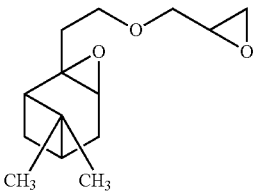
XV

The thermosetting resin compositions of the present invention may be of the one-pack type, in which all the ingredients are mixed together, or of the two-pack type in which the curable component(s), is(are) included in one part and the curing agent is stored separately in a second part, and mix together only prior to use.

During application, the thermosetting resin compositions according to the present invention penetrate and flow readily into the space between the semiconductor chip and the circuit board, or at least show a reduction in viscosity under heated or use conditions thus penetrating and flowing easily.

Generally, it is desirable to prepare thermosetting resin compositions of this invention by selecting the types and proportions of various components to reach a viscosity at a temperature of 25° C. in the range of 500 to 70,000 cps, such as 800 to 20,000 cps, depending on the amount present (if any) of an inorganic filler component, so as to improve its ability to penetrate into the space (e.g., of 10 to 500 μm) between the circuit board and the semiconductor device. At this viscosity, the gel times of the compositions will also be tailored to a specified period of time (such as 15 seconds, or 1 or 2 minutes) at a temperature of about 150° C. In such case, the inventive compositions should show no or substantially no increase of viscosity after a period of time of about six hours. With such a gel time, the compositions penetrate into the space (e.g., of 10 to 500 μm between the circuit board and the semiconductor device relatively rapidly, and allow for a greater number of assemblies to be filled without observing a viscosity increase in the composition thereby rendering it less effective for application.

Reference to FIG. 1 shows a mounted structure (i.e., a FC package) in which a thermosetting resin composition of the present invention has been applied and cured.

The FC package 4 is formed by connecting a semiconductor chip (a bare chip) 2 to a carrier substrate 1 (e.g., a circuit board) and sealing the space therebetween suitably with a thermosetting resin composition 3.

More specifically, for example, in the assembly of FC semiconductor devices using SBB technology, the semiconductor chip 2 may be passed over a substrate bearing a conductive adhesive paste (such as a metal-filled epoxy) to form a layer thereof on the semiconductor chip 2. The layer is ordinarily formed by a printing mechanism. The conductive adhesive paste may be applied on either the carrier substrate or the semiconductor chip. One way to do this is with the stencil claimed and described in International Patent Publication No. PCT/FR95/00898. Alternatively, this connection may also be made by an anisotropically conductive adhesive. See International Patent Publication No. PCT/US97/13677.

Thereafter, the semiconductor chip 2 is positioned over the carrier substrate 1 in such a manner so that the semiconductor chip 2 is in alignment with the electrodes 5 and 6 on the carrier substrate 1, now coated with a patterned layer of conductive adhesive paste or solder, 7 and 8. The conductive adhesive paste may be cured by a variety of ways, though ordinarily a heat cure mechanism is employed.

In order to improve reliability, the space between the semiconductor chip 2 and the carrier substrate 1 is sealed with a thermosetting resin composition 3. The cured product of the thermosetting resin composition should completely fill that space.

The semiconductor chip ordinarily may be coated with a polyimide-, poly-benzocyclobutane- or silicone nitride-based material to passivate environmental corrosion.

Carrier substrates may be constructed from ceramic substrates of $Al_2O_3$, $SiN_3$ and mullite ($Al_2O_3$—$SiO_2$); substrates or tapes of heat-resistant resins, such as polyimides; glass-reinforced epoxy; ABS and phenolic substrates which are also used commonly as circuit boards; and the like. Any electrical connection of the semiconductor chip to the carrier substrate may be used, such as connection by a high-melting solder or electrically (or anisotropically) conductive adhesive and the like. In order to facilitate connections, particularly in SBB technology, the electrodes may be formed as wire bond bumps.

After the semiconductor chip is electrically connected to the carrier substrate, the resulting structure is ordinarily subjected to a continuity test or the like. After passing such test, the semiconductor chip may be fixed thereto with a thermosetting resin composition, as described below. In this way, in the event of a failure, the semiconductor chip may be removed before it is fixed to the carrier substrate with the thermosetting resin composition.

Using a suitable application means, such as a dispenser, a thermosetting resin composition in accordance with this invention is applied to the periphery of the electronically-connected semiconductor chip. The composition penetrates by capillary action into the space between the carrier substrate and the semiconductor chip.

The thermosetting resin composition is then thermally cured by the application of heat. During the early stage of this heating, the thermosetting resin composition shows a significant reduction in viscosity and hence an increase in fluidity, so that it more easily penetrates into the space between the carrier substrate and the semiconductor chip. Moreover, by preheating the carrier substrate, the thermosetting resin composition is allowed to penetrate fully into the entire space between the carrier substrate and the semiconductor chip.

Thermosetting resin compositions of the present invention may ordinarily be cured by heating to a temperature in the range of about 120 to about 180° C. for a period of time of about 0.5 to 30 minutes. However, generally after application of the composition, an initial cure time of about 1 minute sets up the composition, and complete cure is observed after about 5 to about 15 minutes at a temperature of about 165° C. Thus, the composition of the present invention can be used at relatively moderate temperatures and short-time curing conditions, and hence achieve very good productivity.

The amount of thermosetting resin composition applied should be suitably adjusted so as to fill almost completely the space between the carrier substrate and the semiconductor chip, which amount of course may vary depending on application.

Cured reaction products of the thermosetting resin compositions of the present invention demonstrate excellent adhesive force, heat resistance and electric properties, and acceptable mechanical properties, such as flex-cracking resistance, chemical resistance, moisture resistance and the like, for the applications for which they are used herein.

Figure 2:
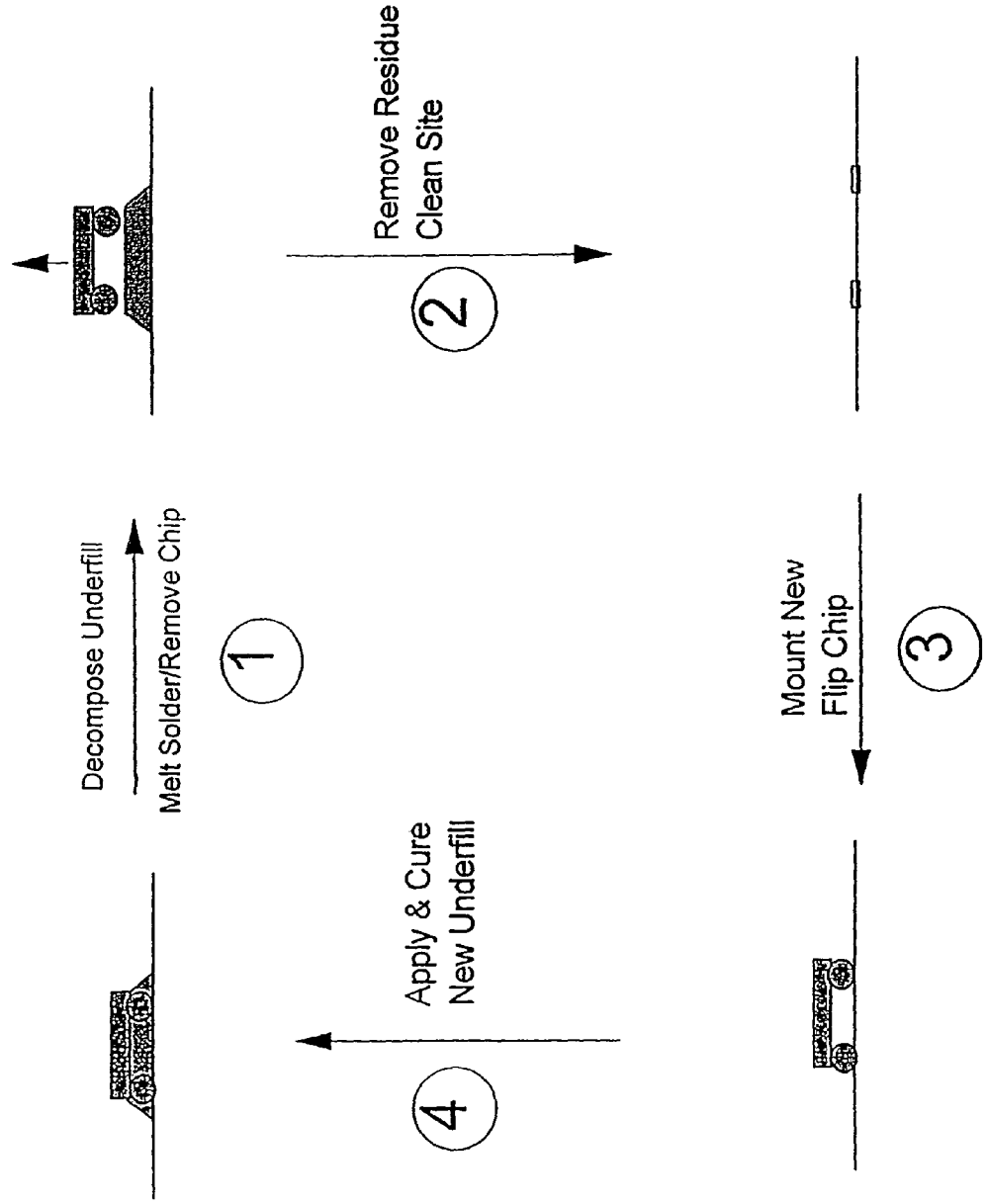
FIG. 2 depicts a flow diagram of a procedure useful to rework a cured thermosetting resin composition in accordance with the present invention, so as to remove a semiconductor device from a circuit board to which it had been attached.

In the mounting process by using the thermosetting resin composition of the present invention, after the semiconductor device is mounted on the circuit board as described above, the resulting structure is tested with respect to characteristics of the semiconductor device, connection between the semiconductor device and the circuit board, other electrical characteristics, and the state of sealing. In the event a failure is found, repair can be made in the following manner and as shown in the flow diagram depicted in FIG. 2.

The area around the semiconductor device which has failed is heated at a temperature of about 190 to about 260° C. for a period of time ranging from about 10 seconds to about 2 minutes. (See FIG. 2, step 1.) Desirably, the temperature should be maintained in the range of about 210 to about 220° C. and the period of time should be within the 30 seconds to 2 minute range. Localized heating is particularly desirable, such as the application of hot air to the failure site by a heating gun.

As soon as the solder is melted and the resin is softened by partial decomposition to cause a reduction in bond strength, the semiconductor device may be pulled apart and removed from the substrate, such as with tweezers or pliers, or through automated processes.

After the semiconductor device 4 is removed, a residue of the cured reaction product of the thermosetting resin composition and a residue of the solder are left on the circuit board 5. The residue of the cured product of the thermosetting resin composition can be removed, for example, by scraping it off after the residue has been softened by heating it to a predetermined temperature. The residue of the solder can be removed, for example, by use of a solder-absorbing braided wire. (See FIG. 2, step 2.) Alternatively, use of a dremel at about 25,000 rpm or more, followed by application of a flat-end horse hair brush, will achieve the desired result.

Finally, a new semiconductor chip may be mounted azain onto the circuit board (which has been cleaned, with fluxing, as described above) in the manner as described above. (See FIG. 2, step 3.) Following mounting, a thermosetting resin composition in accordance with this invention may be dispensed in the area between the semiconductor device and the circuit board, and cured. (See FIG. 2, step 4.) Repair of the failure site is thus completed.

Where a failure site is found in the circuit board, the semiconductor device can be reused by removing the residue of the cured reaction product of the thermosetting resin composition and the residue of the solder left on the bottom of the semiconductor device in the same manner as described above.

The present invention will be more readily appreciated with reference to the examples which follow.

EXAMPLES

Synthesis of Epoxides

Limonene [125 grams (477 mmoles)] and methylene chloride (1000 ml) were added to a reaction flask, and the resulting solution cooled with an ice bath to a temperature in the range of about 0 to about 10° C. Then, 70% m-chloroperbenzoic acid [259.5 grams (1050 mmoles)] was added with stirring in small increments over a period of time of about 110 minutes, while maintaining the temperature of the reaction mixture below about 15° C. The reaction mixture was stirred overnight, while maintaining the temperature below about 15° C. m-Chlorobenzoic acid was formed as a precipitate, and filtered off, with the organic filtrate washed twice with 500 ml portions of 10% aqueous $Na_2SO_3$, twice with 500 ml portions of saturated aqueous $Na_2CO_3$ solution, and twice with 500 ml portions of water. The organic layer was separated, dried over anhydrous $MgSO_4$, and then filtered. Basic alumina (50 grams) was then added to the organic filtrate, with the mixture stirred for a period of time of about 45 minutes, and then filtered. The organic solvent was removed under reduced pressure, and the resulting product vacuum distilled. Limonene diepoxide was obtained in an amount of 120.7 grams (86% yield). $^1$H NMR (CDCl$_3$) 3.0 (m, 1, C°C—H), 2.5 (m, 2, C°C—H), 1.0-2.2 (m, 7, CH, CH$_2$), 1.3 (s, 3, ring CH$_3$), 1.2 (m, 3, side-chain CH$_3$); IR (neat) 2932, 1436, 1381, 853, 763 cm$^{-1}$.

Gamma-terpinene diepoxide, methyl cyclopentadiene dimer diepoxide and ethylidene norbornene diepoxide were prepared in the same manner. Their spectral data are given as follows: $^1$H NMR (CDCl$_3$) 2.5-3.0 (m, 2, C°C—H), 2.1 (m, 4, CH$_2$), 1.6 (m, 1, CH), 1.3 (s, 3, CH$_3$), 1.0 (m, 6, side-chain CH$_3$); IR (neat) 2963, 1467, 1107, 834, 709 cm$^{-1}$; $^1$H NMR (CDCl$_3$) 3.0-3.5 (m, 1, C°C—H), 2.5-2.7 (m, 1.5, C°C—H), 1.2-1.9 (m, 8, CH, CH$_2$), 1.4-1.5 (m, 6, CH$_3$); IR (neat) 2956, 1448, 1078, 829, 759 cm$^{-1}$; and $^1$H NMR (CDCl$_3$) 3.0-3.5 (m, 2, C°C—H), 3.0-3.5 (br s, 1, C°C—H), 1.1-2.3 (m, 6, CH, CH$_2$), 1.3 (d, 3, CH$_3$); IR (neat) 2979, 1449, 1376, 1008, 852, 757 cm$^{-1}$, respectively.

The yields and boiling points of these diene diepoxides are given below in Table 1.

TABLE 1

Yields and Boiling Points of Certain Diene Diepoxides

| Physical Properties | Limonene Diepoxide | γ-Terpinene Diepoxide | MCPD Dimer Diepoxide | ENB Diepoxide |
|---|---|---|---|---|
| Distillation Temperature (° C.) | 68-70 | — | 90-100 | 65-67 |
| Distillation Pressure (mTorr) | 850 | — | 780 | 850 |
| Crude Yield (%) | 89 | Quantitative | 93.7 | 96.2 |
| Distilled Yield (%) | 61 | — | 75.3 | 71.8 |
| Physical Appearance | Clear liquid | Opaque liquid | Friable solid | Clear liquid |
| GC (% Purity) | 98.3 | — | 96.3 | 99.3 |

Figure 15:
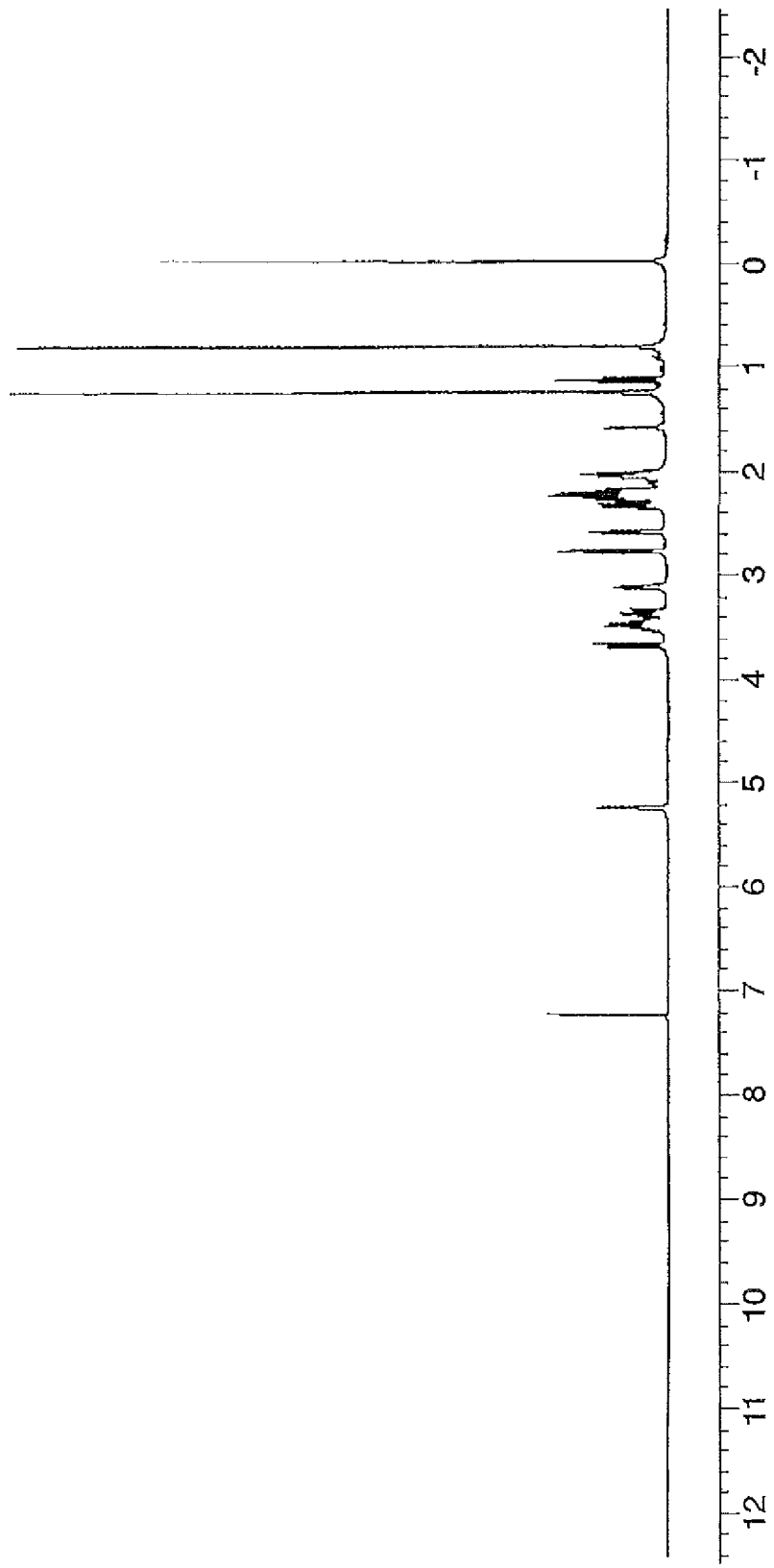
FIG. 15 depicts a $^1$H HMR spectra of nopol glycidyl ether.
Figure 16:
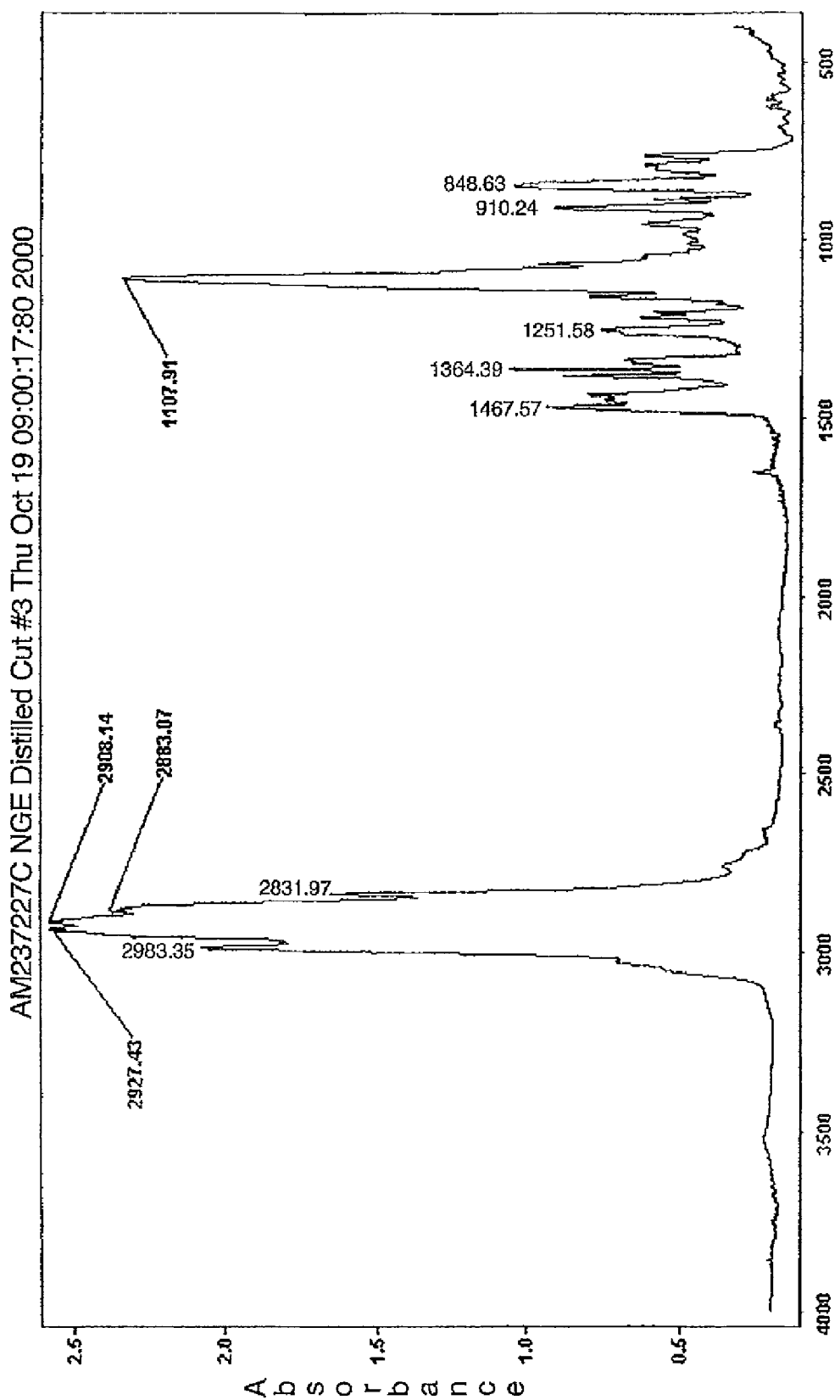
FIG. 16 depicts a FT-IR spectra of nopol glycidyl ether.

Nopol epoxide glycidyl ether was prepared as follows:

To a four-necked 1000 ml reaction flask, equipped with a mechanical stirrer, thermometer, and condenser, was added 200 ml of 50 weight percent aq. NaOH, epibromohydrin (144.3 g, 1.03 mol), and tetrabutylammonium hydrogen sulfate (4.2 g, 12 mmol). The mixture was stirred vigorously at room temperature for a period of time of about 20 minutes to a pale yellow color. The mixture was then cooled to a temperature of about 10° C. in an ice/water bath. To the mixture was added (1R)-(−)-nopol (50 g, 295 mmol) dropwise over a period of time of about 30 minutes. The reaction temperature was maintained at or near about 10° C. during the addition. The ice/water bath was removed, and the mixture was allowed to warm to ambient temperature, while it stirred overnight. The reaction mixture was then quenched with 500 ml of ice cold water, which was added over a period of time of about 15 minutes, with stirring for an additional period of time of about 20 minutes. The mixture was transferred to a 2 liter separatory funnel, where it was twice extracted with 200 ml of diethyl ether. The organic portion was then washed twice with 200 ml of sat. aq. NaCl, separated, dried over anhydrous MgSO$_4$, and then filtered. After filtration, the solvent was removed under reduced pressure. The crude product was vacuum distilled to yield about 48.1 g (74%) yield of nopol glycidyl ether, with a boiling point of about 94-96° C. at atmospheric pressure. The spectral data are given as follows: $^1$H NMR (CDCl$_3$) 5.25 (br s, 1, =CH), 2.8-3.7 (m, 7, OCH, OCH$_2$), 2.0-2.4 (m, 6, CH, CH$_2$), 1.6 (s, 1, CH), 1.3 (s, 3, CH$_3$), 1.1 (d, 1, CH), 0.8 (s, 3, CH$_3$) (see FIG. 15); FT-IR 2927, 2908, 1468, 1364, 1108, 910, 849 cm$^{-1}$ (see FIG. 16).

Figure 17:
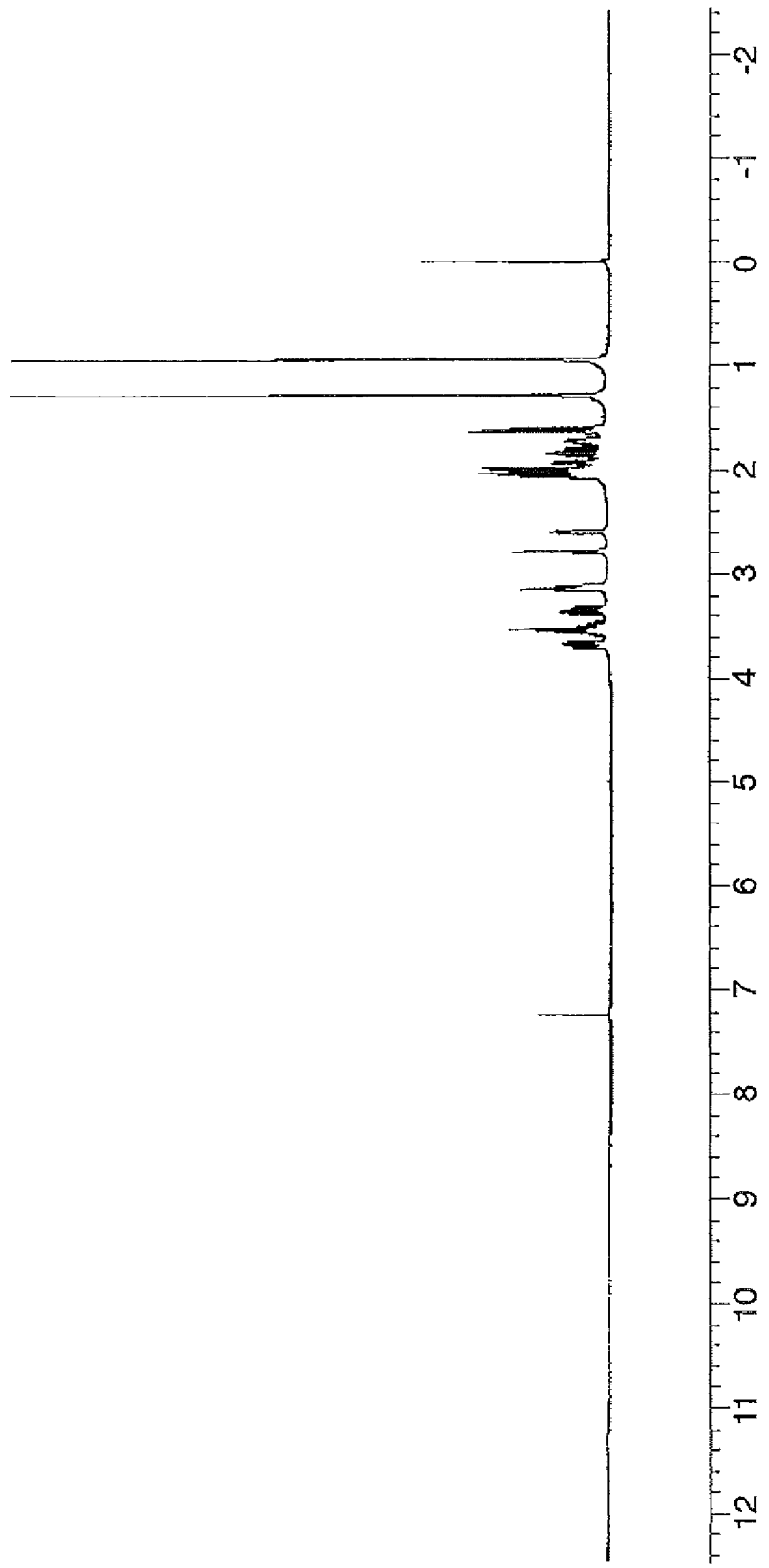
FIG. 17 depicts a $^1$H HMR spectra of nopol epoxide glycidyl ether.
Figure 18:
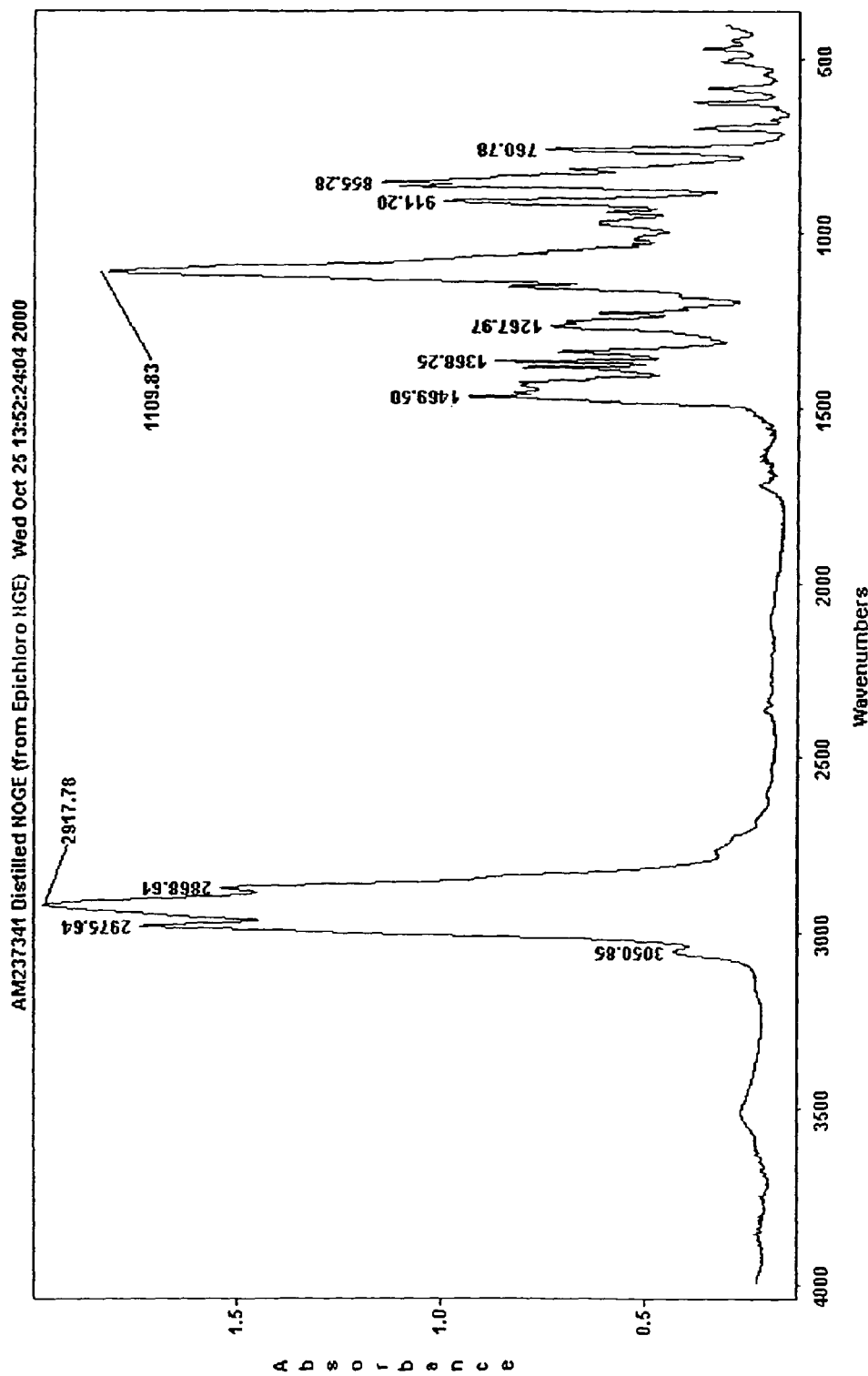
FIG. 18 depicts a FT-IR spectra of nopol epoxide glycidyl ether.

To a four-necked 500 ml flask equipped with a mechanical stirrer, thermometer, and condenser, was added nopol glycidyl ether (48.2 g, 205.4 mmol), and methylene chloride (250 ml). To the solution was added 70% m-chloroperoxybenzoic acid (53 g, 215 mmol) over a period of time of about 2 hours. The reaction temperature was maintained below about 15° C. with an ice/water bath during the addition. After the addition was complete, the reaction mixture was stirred overnight and maintained at a temperature below about 20° C. with an ice water bath. m-Chlorobenzoic acid was formed as a precipitate, and filtered the organic filtrate washed off, twice with 200 ml portions of 10% aq. Na$_2$SO$_3$, twice with 200 ml portions sat. aq. NaHCO$_3$, and twice with 200 ml portions of water. The organic layer was separated, dried over anhydrous MgSO$_4$, and filtered. Solvent was removed under reduced pressure, and the crude product was vacuum distilled. Nopol epoxide glycidyl ether was obtained in a yield of about 46.5 g (91%), with a boiling point of about 110-113° C. at 800 mTorr. $^1$H NMR (CDCl$_3$) 2.8-3.7 (m, 8, OCH, OCH$_2$), 2.0-2.4 (m, 8, CH, CH$_2$), 1.3 (s, 3, CH$_3$) (see FIG. 17), 0.9 (s, 3, CH$_3$); FT-IR 2917, 1470, 1110, 911, 855, 761 cm$^{-1}$ (see FIG. 18).

Thermosetting Resin Compositions

Preparation

A thermosetting resin composition (Sample No. 1) was prepared by mixing together for a period of time of about 10 minutes at room temperature in an open vessel the following components:
1. an epoxy resin component including
   51.7 weight percent of limonene diepoxide prepared as above, and
2. a curing agent component including
   46.5 weight percent of MHHPA,
   0.8 weight percent of benzyldimethyl amine, and
   1 weight percent of ethylene glycol.

Four additional compositions (Samples Nos. 2-5) were prepared in this manner, substituting for the limonene diepoxide, the same amounts of gamma-terpinene diepoxide, Compound XVI of the '922 patent, and the commercially available epoxy resins, ERL-4221 and RE-404-S. [See Table 2(a).]

A further thermosetting resin composition (Sample No. 6) was prepared as described above by mixing together the following components:
1. an epoxy resin component including
   51.7 weight percent of limonene diepoxide, and
2. a curing agent component including
   4.7 weight percent of dicyandiamide, and
   1.9 weight percent of an imidazole (commercially available from Synthron, Inc. under the trade designation "ACTIRON" NXJ-60).

Four additional compositions (Samples Nos. 7-10) were prepared as Sample No. 6, substituting for the limonene diepoxide, the same amounts of gamma-terpinene diepoxide, Compound XVI of the '922 patent, and the commercially available epoxy resins ERL-4221 and RE-404-S. [See Table 2(a).]

TABLE 2(a)

| Component | | Sample No./Amount (weight percent) | | | | | | | | | |
|---|---|---|---|---|---|---|---|---|---|---|---|
| Type | Identity | 1 | 2 | 3 | 4 | 5 | 6 | 7 | 8 | 9 | 10 |
| Epoxy Resin | Limonene Diepoxide | 51.7 | — | — | — | — | 93.4 | — | — | — | — |
| | Terpinene Diepoxide | — | 51.7 | — | — | — | — | 93.4 | — | — | — |
| | ERL-4221 | — | — | — | 51.7 | — | — | — | — | 93.4 | — |
| | Compound XVI | — | — | 51.7 | — | — | — | — | 93.4 | — | — |
| | RE-404-S | — | — | — | — | 51.7 | — | — | — | — | 93.4 |
| Curing Agent | NXJ-60 (Imidazole) | — | — | — | — | — | 1.9 | 1.9 | 1.9 | 1.9 | 1.9 |
| | 1B2MZ (Imidazole) | — | — | — | — | — | — | — | — | — | — |
| | CG-1400 (Dicyandiamide) | — | — | — | — | — | 4.7 | 4.7 | 4.7 | 4.7 | 4.7 |
| | MHHPA (Anhydride) | 46.5 | 46.5 | 46.5 | 46.5 | 46.5 | — | — | — | — | — |
| | Benzyldimethyl amine | 0.8 | 0.8 | 0.8 | 0.8 | 0.8 | — | — | — | — | — |
| | Ethylene glycol | 1 | 1 | 1 | 1 | 1 | — | — | — | — | — |

A further thermosetting resin composition (Sample No. 11) was prepared with a limonene diepoxide/RE-404-S combination, designed with an imidazole/dicyandiamide cure, as described above by mixing together the following components:

1. an epoxy resin component including
   74.7 weight percent of limonene diepoxide, and
   18.7 weight percent of RE-404-S, and
2. a curing agent component including
   4.7 weight percent of dicyandiamide, and
   1.9 weight percent of the imidazole, NXJ-60.

Two additional compositions (Samples Nos. 12-13) were prepared as Sample No. 11, except that the weight percent of the limonene diepoxide was decreased and the weight percent of the RE-404-S was increased. [See Table 2(b).]

A still further thermosetting resin composition (Sample No. 14) was prepared with a terpinene diepoxide/RE-404-S combination, designed with an imidazole/dicyandiamide cure, as described above by mixing together the following components:

1. an epoxy resin component including
   74.7 weight percent of terpinene diepoxide, and
   18.7 weight percent of RE-404-S, and
2. a curing agent component including
   4.7 weight percent of dicyandiamide, and
   1.9 weight percent of the imidazole, NXJ-60.

Two additional compositions (Samples Nos. 15-16) were prepared as Sample No. 14, except that the weight percent of the terpinene diepoxide was decreased and the weight percent of the RE-404-S was increased. [See Table 2(b).]

An additional thermosetting resin composition (Sample No. 17) was prepared based on a limonene diepoxide/RE-404-S combination, designed with an imidazole/dicyandiamide cure, as described above by mixing together the following components:

1. an epoxy resin component including
   39.17 weight percent of limonene diepoxide, and
   26.11 weight percent of RE-404-S;
2. a curing agent component including
   1.4 weight percent of the imidazole, NXJ-60, and
   3.14 weight percent of dicyandiamide;
3. 30 weight percent of an inorganic filler component, S0-E5 silica; and
4. a flowability agent including
   the silanes, octyl (A-137, 0.06 weight percent) and glycidyl (A-187, 0.06 weight percent), and
   titanate (KR-55, 0.06 weight percent).

Five additional compositions (Sample Nos. 18-21 and 25) were prepared along these lines, except that the limonene diepoxide/RE-404-S ratio was varied, and as to Sample Nos. 21 and 25, the weight percents of the components of the flowability agent were also varied. [See Tables 2(b) and 2(c).]

TABLE 2(b)

| Component | | Sample No./Amount (weight percent) | | | | | | | | | |
|---|---|---|---|---|---|---|---|---|---|---|---|
| Type | Identity | 11 | 12 | 13 | 14 | 15 | 16 | 17 | 18 | 19 | 20 |
| Epoxy Resin | Limonene Diepoxide | 74.7 | 65.4 | 56 | — | — | — | 39.17 | 32.64 | 26.11 | 19.58 |
| | Terpinene Diepoxide | — | — | — | 74.7 | 65.4 | 56 | — | — | — | — |
| | RE-404-S | 18.7 | 28 | 37.4 | 18.7 | 28 | 37.4 | 26.11 | 32.64 | 39.17 | 45.70 |
| | BEO-60E | — | — | — | — | — | — | — | — | — | — |
| Inorganic Filler | SO-ES (Silica) | — | — | — | — | — | — | 30 | 30 | 30 | 30 |
| Curing Agent | NXJ-60 (Imidazole) | 1.9 | 1.9 | 1.9 | 1.9 | 1.9 | 1.9 | 1.4 | 1.4 | 1.4 | 1.4 |
| | 1B2MX (Imidazole) | — | — | — | — | — | — | — | — | — | — |
| | CG-1400 (Dicyandiamide) | 4.7 | 4.7 | 4.7 | 4.7 | 4.7 | 4.7 | 3.14 | 3.14 | 3.14 | 3.14 |

TABLE 2(b)-continued

| Component | | Sample No./Amount (weight percent) | | | | | | | | | |
|---|---|---|---|---|---|---|---|---|---|---|---|
| Type | Identity | 11 | 12 | 13 | 14 | 15 | 16 | 17 | 18 | 19 | 20 |
| Flowability Agent | A-137 (Silane) | — | — | — | — | — | — | 0.06 | 0.06 | 0.06 | 0.06 |
| | A-187 (Silane) | — | — | — | — | — | — | 0.06 | 0.06 | 0.06 | 0.06 |
| | KR-55 (Titanate) | — | — | — | — | — | — | 0.06 | 0.06 | 0.06 | 0.06 |
| Pigment | Red | — | — | — | — | — | — | — | — | — | — |

A further additional thermosetting resin composition (Sample No. 22) was prepared based on a limonene diepoxide/RE-404-S combination, designed with an anhydride cure, as described above by mixing together the following components:

1. an epoxy resin component including
  10.83 weight percent of limonene diepoxide, and
  16.24 weight percent of RE-404-S;
2. a curing agent component including
  24.36 weight percent of LINDRIDE 62C,
  2.71 weight percent of B-4400, and
  0.11 weight percent of the imidazole, NXJ-60;
3. 45 weight percent of an inorganic filler component, S0-E5 silica;
4. a flowability agent including
  the silanes (A-137, 0.09 weight percent) and (A-187, 0.12 weight percent), and
  titanate (KR-55, 0.45 weight percent); and
5. 0.1 weight percent of red pigment.

Two additional compositions (Sample Nos. 23-24) were prepared along these lines, except that the limonene diepoxide/RE-404-S ratio was varied, the weight percents of the components of the anhydride cure agent were also varied, and the weight percent of the inorganic filler component were varied as well. [See Table 2(c).]

Yet a further additional thermosetting resin composition (Sample No. 26) was prepared based on a limonene diepoxide (commercially available from Daicel Chem. Co., Ltd., Japan under the tradename "CELLOXIDE" 3000), designed to cure with a latent hardener (commercially available from Asahi-Ciba, Ltd., Japan under the tradename "NOVACURE" HX-3921 HP), and without a second epoxy resin, as described above by mixing together the following components:

1. an epoxy resin component including
  40 weight percent of limonene diepoxide; and
2. a curing agent component including
  60 weight percent of "NOVACURE" HX-3921 HP.

Four additional compositions (Sample Nos. 27-30) were prepared along these lines, except that the limonene diepoxide/latent hardener ratio was varied, and an inorganic filler component was included in various weight percents, and a second epoxy resin was included in Sample No. 30. [See Table 2(c).]

TABLE 2(c)

| Component | | Sample No./Amount (weight percent) | | | | | | | | | |
|---|---|---|---|---|---|---|---|---|---|---|---|
| Type | Identity | 21 | 22 | 23 | 24 | 25 | 26 | 27 | 28 | 29 | 30 |
| Epoxy Resin | Limonene Diepoxide | 26.09 | 10.83 | 12.12 | 8.58 | 19.50 | 40 | 28 | 24 | 20 | 12 |
| | RE-404-S | 39.14 | 16.24 | 22.52 | 15.92 | 45.50 | — | — | — | — | — |
| | BEO-60E | — | — | — | — | — | — | — | — | — | 12 |
| Inorganic Filler | SO-ES (Silica) | 30 | 45 | 30 | 50 | 30 | — | 30 | 40 | 50 | 40 |
| Curing Agent | NXJ-60 (Imidazole) | 1.4 | — | — | — | 1.39 | — | — | — | — | — |
| | 1B2MZ (Imidazole) | — | 0.11 | 0.14 | 0.098 | — | — | — | — | — | — |
| | CG-1400 (Dicyandiamide) | 3.14 | — | — | 3.13 | — | — | — | — | — | — |
| | LINDRIDE 62C (Anhydride) | — | 24.36 | 34.64 | 20.82 | — | — | — | — | — | — |
| | B-4400 (Anhydride) | — | 2.71 | — | 3.68 | — | — | — | — | — | — |
| | NOVACURE HX-3921 HP (Latent hardener) | — | — | — | — | — | 60 | 42 | 36 | 30 | 36 |
| Flowability Agent | A-137 (Silane) | 0.06 | 0.09 | 0.06 | 0.10 | 0.06 | — | — | — | — | — |
| | A-187 (Silane) | 0.12 | 0.12 | 0.12 | 0.20 | 0.12 | — | — | — | — | — |
| | KR-55 (Titanate) | 0.06 | 0.45 | 0.30 | 0.50 | 0.30 | — | — | — | — | — |
| Pigment | Red | — | 0.1 | 0.1 | 0.1 | — | — | — | — | — | — |

TABLE 2(d)

| Component Type | Identity | 31 | 32 | 33 | 34 | 35 | 36 | 37 | 38 | 39 | 40 |
|---|---|---|---|---|---|---|---|---|---|---|---|
| Epoxy Resin | Limonene Diepoxide | — | — | 12.12 | 8.58 | 19.50 | 40 | 28 | 24 | 20 | 12 |
| | RE-404-S | — | — | 22.52 | 15.92 | 45.50 | — | — | — | — | — |
| | Ethylidene Norbornene Diepoxide | 51.7 | — | — | — | — | — | — | — | — | — |
| | Methyl Cyclopentadiene Dimer Diepoxide | — | 51.7 | — | — | — | — | — | — | — | — |
| Inorganic Filler | SO-ES (Silica) | — | — | 30 | 50 | 30 | — | 30 | 40 | 50 | 40 |
| Curing Agent | NXJ-60 (Imidazole) | — | — | — | — | 1.39 | — | — | — | — | — |
| | 1B2MZ (Imidazole) | — | — | 0.14 | 0.098 | — | — | — | — | — | — |
| | CG-1400 (Dicyandiamide) | — | — | — | 3.13 | — | — | — | — | — | — |
| | MHHPA (Anhydride) | 46.5 | 46.5 | — | — | — | — | — | — | — | — |
| | LINDRIDE 62C (Anhydride) | — | — | 34.64 | 20.82 | — | — | — | — | — | — |
| | B-4400 (Anhydride) | — | — | — | 3.68 | — | — | — | — | — | — |
| | NOVACURE HX-3921 HP (Latent hardener) | — | — | — | — | — | 60 | 42 | 36 | 30 | 36 |
| | Benzyldimethyl amine | 0.9 | 0.9 | — | — | — | — | — | — | — | — |
| | Ethylene glycol | 1 | 1 | — | — | — | — | — | — | — | — |
| Flowability Agent | A-137 (Silane) | — | — | 0.06 | 0.10 | 0.06 | — | — | — | — | — |
| | A-187 (Silane) | — | — | 0.12 | 0.20 | 0.12 | — | — | — | — | — |
| | KR-55 (Titanate) | 0.06 | 0.45 | 0.30 | 0.50 | 0.30 | — | — | — | — | — |
| Pigment | Red | — | 0.1 | 0.1 | 0.1 | — | — | — | — | — | — |

Sample Nos. 31 and 32 show thermosetting resin compositions prepared from ethylidene norbornene diepoxide and methyl cyclopentadiene dimer diepoxide, respectively, designed to cure with an anhydride curing agent. Sample Nos. 33-35 show thermosetting resin compositions, based on limonene diepoxide/RE-404-S in combination at various ratios (like Sample Nos. 21-25) designed to cure with an anhydride curing agent, an imidizole curing agent, or both. Sample Nos. 36-40 show thermosetting resin compositions based on limonene diepoxide designed to cure with a latent hardener (commercially available for Asahi-Ciba, Ltd., Japan under the tradename "NOVACURE" HX03921 HP), with and without an inorganic filler. [See Table 2(d).]

Yet a further additional thermosetting resin composition (Sample No. 41) was prepared based on a limonene diepoxide (commercially available from Daicel Chem. Co., Ltd., Japan under the tradename "CELLOXIDE" 3000), designed to cure with a latent hardener (commercially available from Asahi-Ciba, Ltd., Japan under the tradename "NOVACURE" HX-3921 HP), without a second epoxy resin, as described above by mixing together the following components:

1. an epoxy resin component including 40 weight percent of limonene diepoxide; and 2. a curing agent component including 60 weight percent of "NOVACURE" HX-3921 HP.

Nine additional compositions (Sample Nos. 42-49) were prepared along these lines, except that the type and amount of the epoxy resin was varied as noted, and an inorganic filler component was included in various weight percents, and a second epoxy resin was included in Sample Nos. 43 and 46-49, with a third epoxy resin being including in Sample Nos. 47 and 48. [See Table 2(e).]

TABLE 2(e)

| Component Type | Identity | 41 | 42 | 43 | 44 | 45 | 46 | 47 | 48 | 49 |
|---|---|---|---|---|---|---|---|---|---|---|
| Epoxy Resin | Limonene Diepoxide | — | — | — | — | — | — | 2.79 | 2.76 | — |
| | Nopol Diepoxide | — | — | — | — | — | 26.11 | 19.55 | 19.33 | 11.81 |
| | RE-404-S | — | 39.17 | 21.60 | 39.17 | 21.60 | 39.17 | 33.52 | 33.14 | 21.92 |
| | Ethylidene Norbornene Diepoxide | 51.7 | — | 26.11 | — | 11.43 | — | — | — | — |
| | Methyl Cyclopentadiene Dimer Diepoxide | — | 26.11 | 11.64 | — | — | — | — | — | — |
| Inorganic Filler | SO-ES (Silica) | — | 30 | 30 | 30 | 30 | 30 | 40 | 40 | 30 |

TABLE 2(e)-continued

| Component | | Sample No./Amount (weight percent) | | | | | | | | |
|---|---|---|---|---|---|---|---|---|---|---|
| Type | Identity | 41 | 42 | 43 | 44 | 45 | 46 | 47 | 48 | 49 |
| Curing Agent | NXJ-60 (Imidazole) | — | 1.4 | — | 1.4 | — | 1.4 | 1.2 | 1.18 | — |
| | 1B2MZ (Imidazole) | — | — | 0.14 | — | 0.14 | — | — | — | 0.14 |
| | CG-1400 (Dicyandiamide) | — | 3.14 | — | 3.14 | — | 3.14 | 2.69 | 2.66 | — |
| | MHHPA (Anhydride) | 46.5 | — | — | — | — | — | — | — | — |
| | LINDRIDE 62C (Anhydride) | — | — | 36.09 | — | 36.71 | — | — | — | 35.57 |
| | Benzyldimethyl Amine | 0.9 | — | — | — | — | — | — | — | — |
| | Ethylene glycol | 1 | — | — | — | — | — | — | — | — |
| Flowability Agent | A-137 (Silane) | — | 0.06 | 0.05 | 0.06 | 0.05 | 0.06 | 0.08 | 0.4 | 0.05 |
| | A-187 (Silane) | — | 0.06 | 0.26 | 0.06 | 0.12 | 0.08 | 0.08 | 0.12 | 0.12 |
| | KR-55 (Titanate) | 0.06 | 0.06 | 0.30 | 0.06 | 0.25 | 0.06 | 0.8 | 0.4 | 0.27 |
| Pigment | Red | — | 0.1 | 0.1 | 0.1 | 0.1 | 0.1 | — | — | — |

In Table 2(f) below, combinations of RE-404-S together with either methyl cyclopentadiene dimer diepoxide, ethylidene norbornene diepoxide or nopol epoxide dylycidyl ether, at different ratios are presented as Sample Nos. 50-58, designed to cure with anhydride curing agents, and Sample No. 59, which is nopol epoxy glycidyl ether cured with an anhydride curing agent.

TABLE 2(f)

| Component | | Sample No./Amount (weight percent) | | | | | | | | | |
|---|---|---|---|---|---|---|---|---|---|---|---|
| Type | Identity | 50 | 51 | 52 | 53 | 54 | 55 | 56 | 57 | 58 | 59 |
| Epoxy Resin | Limonene Diepoxide | — | — | — | — | — | — | — | — | — | — |
| | Nopol Diepoxide | — | — | — | — | — | — | 41.35 | 31 | 20.7 | 51.7 |
| | RE-404-S | 10.35 | 20.7 | 31 | 10.35 | 20.7 | 31 | 10.35 | 20.7 | 31 | — |
| | Ethylidene Norbornene Diepoxide | — | — | — | 41.35 | 31 | 20.7 | — | — | — | — |
| | Methyl Cyclopentadiene Dimer Diepoxide | 41.35 | 31 | 20.7 | — | — | — | — | — | — | — |
| Inorganic Filler | SO-ES (Silica) | — | — | — | — | — | — | — | — | — | — |
| Curing Agent | NXJ-60 (Imidazole) | — | — | — | — | — | — | — | — | — | — |
| | 1B2MZ (Imidazole) | — | — | — | — | — | — | — | — | — | — |
| | CG-1400 (Dicyandiamide) | — | — | — | — | — | — | — | — | — | — |
| | MHHPA (Anhydride) | 46.5 | 46.5 | 46.5 | 46.5 | 46.5 | 46.5 | 46.5 | 46.5 | 46.5 | 46.5 |
| | LINDRIDE 62C (Anhydride) | — | — | — | — | — | — | — | — | — | — |
| | Benzyldimethyl Amine | 0.8 | 0.8 | 0.8 | 0.8 | 0.8 | 0.8 | 0.8 | 0.8 | 0.8 | 0.8 |
| | Ethylene glycol | 1 | 1 | 1 | 1 | 1 | 1 | 1 | 1 | 1 | 1 |
| Flowability Agent | A-137 (Silane) | — | — | — | — | — | — | — | — | — | — |
| | A-187 (Silane) | — | — | — | — | — | — | — | — | — | — |
| | KR-55 (Titanate) | — | — | — | — | — | — | — | — | — | — |
| Pigment | Red | — | — | — | — | — | — | — | — | — | — |

Shelf-Stability

While the compositions were used upon formation (see below), they may be stored for a period of time of up to about 3 to about 6 months at a temperature of about −40° C. without experiencing viscosity increase.

After formation, the composition was transferred to a 10 ml syringe made of non-reactive plastic.

Mounting/Underfill Process

Using cream solder (PS10R-350A-F92C; manufactured by Harima Chemicals, Inc.), a CSP having a package of 20 mm square, an electrode diameter of 0.5 mm, an electrode pitch of 11.0 mm, and a carrier substrate made of alumina was mounted on a 1.6 mm thick glass-reinforced epoxy board having a circuit formed thereon.

Certain of the samples (Sample Nos. 17-25) were dispensed through a 12G needle connected to the syringe into the junction between the carrier substrate and semiconductor device an assembly previously formed as above.

After such dispensing, the assembly was transferred to an oven while the temperature was maintained at about 165° C. The composition cured initially after about 1 minute, and thereafter cured completely after about 15 minutes at that temperature.

Rather than using all the samples as underfill sealants, certain of them (Sample Nos. 1-16) were dispensed onto an aluminum dish, and cured in a step-wise manner by exposure to an elevated temperature of about 100° C. for a period of time of about 2 hours, followed by exposure to an elevated temperature of about 140° C. for a period of time of about 6 hours, at the end of which time the compositions were observed to have cured.

Physical Properties

The compositions have a variety of properties in both the uncured and cured state which are measurable and useful parameters for the end user in choosing a particular formulation for a desired need.

For instance, in the uncured state, the flow rate is of interest; in reaching the cured state, the cure schedule is of interest.

The flow time allows the end user to determine the rapidity with which the adhesive may be applied during a fabrication process, such as a circuit assembly operation. It may be measured by passing the composition through a 25 μm gap between glass slides aligned perpendicular to one another, using metal shims as spacers. The time required for the composition to flow between the slides is then measured at a length of about one inch, at 0.25 inch intervals. Values in seconds for the flow times of the compositions set forth above are presented as an average of three measurements below in Table 3.

The cure schedule refers to the time required for the onset of cure to occur at a certain temperature, in a specified period of time. This may be seen in more detail with regard to certain of the samples prepared in accordance with the present invention below in Table 3.

TABLE 3

| Sample No. | Physical Properties | |
|---|---|---|
| | Flow Time (secs, .5" @100° C.) | Cure Schedule (mins@165° C.) |
| 17 | — | 10-15 |
| 18 | — | 10-15 |
| 19 | 18 | 10-15 |
| 20 | — | 10-15 |
| 21 | 15 | 10-15 |
| 22 | 35 | 10-15 |
| 23 | 13 | 10-15 |
| 24 | 28 | 10-15 |
| 25 | 18 | 10-15 |
| 47 | 22 | — |
| 48 | 10 | — |

As the composition progresses through its cure schedule, the reaction exotherm, or enthalpy, assists in determining the effectiveness of a (co)polymerization reaction. The reaction exotherm here is measured by differential scanning calorimetry ("DSC").

The peak temperature ("$T_{PEAK}$") and onset temperature ("$T_{ONSET}$") may be determined from the DSC measurement. These values provide information for minimum reasonable curing temperatures, the curing temperature range, maximum reaction temperatures, and relative curing time at each temperature. See Tables 4, 4(b) and 4(c).

TABLE 4(a)

| | Physical Properties | | |
|---|---|---|---|
| Sample No. | Enthalpy (J/g) | $T_{PEAK}$ | $T_{ONSET}$ |
| 1 | 266 | 175 | 133 |
| 2 | — | — | — |
| 3 | 70 | 178 | 156 |
| 4 | 61 | 167 | 140 |
| 5 | 171 | 162 | 124 |

TABLE 4(b)

| | Physical Properties | | |
|---|---|---|---|
| Sample No. | Enthalpy (J/g) | $T_{PEAK}$ | $T_{ONSET}$ |
| 17 | 229.7 | 141.1 | 128.9 |
| 18 | 249.7 | 138.3 | 125.4 |
| 19 | 280.3 | 135.8 | 122.1 |
| 20 | 315.1 | 133.6 | 120.7 |
| 21 | 287.2 | 136.3 | 123.5 |

TABLE 4(c)

| | Physical Properties | | |
|---|---|---|---|
| Sample No. | Enthalpy (J/g) | $T_{PEAK}$ | $T_{ONSET}$ |
| 31 | — | — | — |
| 32 | 234 | 164 | 123 |
| 41 | 395 | 162 | 85 |
| 42 | 234 | 136 | 122 |
| 43 | 171 | 171 | 142 |
| 44 | 228 | 135 | 120 |
| 45 | 252 | 166 | 134 |
| 46 | 326 | 153 | 121 |
| 49 | 262 | 168 | 131 |

In the cured state, a variety of properties are useful depending on the end use for which the composition is destined.

For instance, adhesion provides information on the strength of the bond formed by the cured reaction product, data for which is set forth in Table 5. In this adhesion evaluation, die shear adhesion is measured by a Sebastion 5 die shear measurement instrument, which measures the amount of shear strength (in Kgf) required to pull apart a die attached to a circuit board by the cured reaction product as an underfill sealant (without a solder mask, or chipbonding adhesive).

TABLE 5

| Sample No./ (mg/die) | Adhesion (Die Shear, Kgf) |
|---|---|
| 17 (3) | 100 |
| 19 (3) | 115 |
| 20 (3) | 126 |
| 17 (1-1.5) | 30 |
| 19 (1-1.5) | 80 |
| 20 (1-1.5) | 75 |
| 42 (1-1.5) | 34 |
| 44 (1-1.5) | 29 |
| 46 (1-1.5) | 29 |
| 47 (1-1.5) | 36 |
| 48 (1-1.5) | 36 |

Reworkability determines the ease with which a cured reaction product may be controllably degraded. The extent to which the cured reaction product loses mass over time at an increase in temperature may be measured by thermal gravimetric analysis ("TGA"), and provides information on the temperature (or range) at which the cured reaction product degrades.

Figure 3:
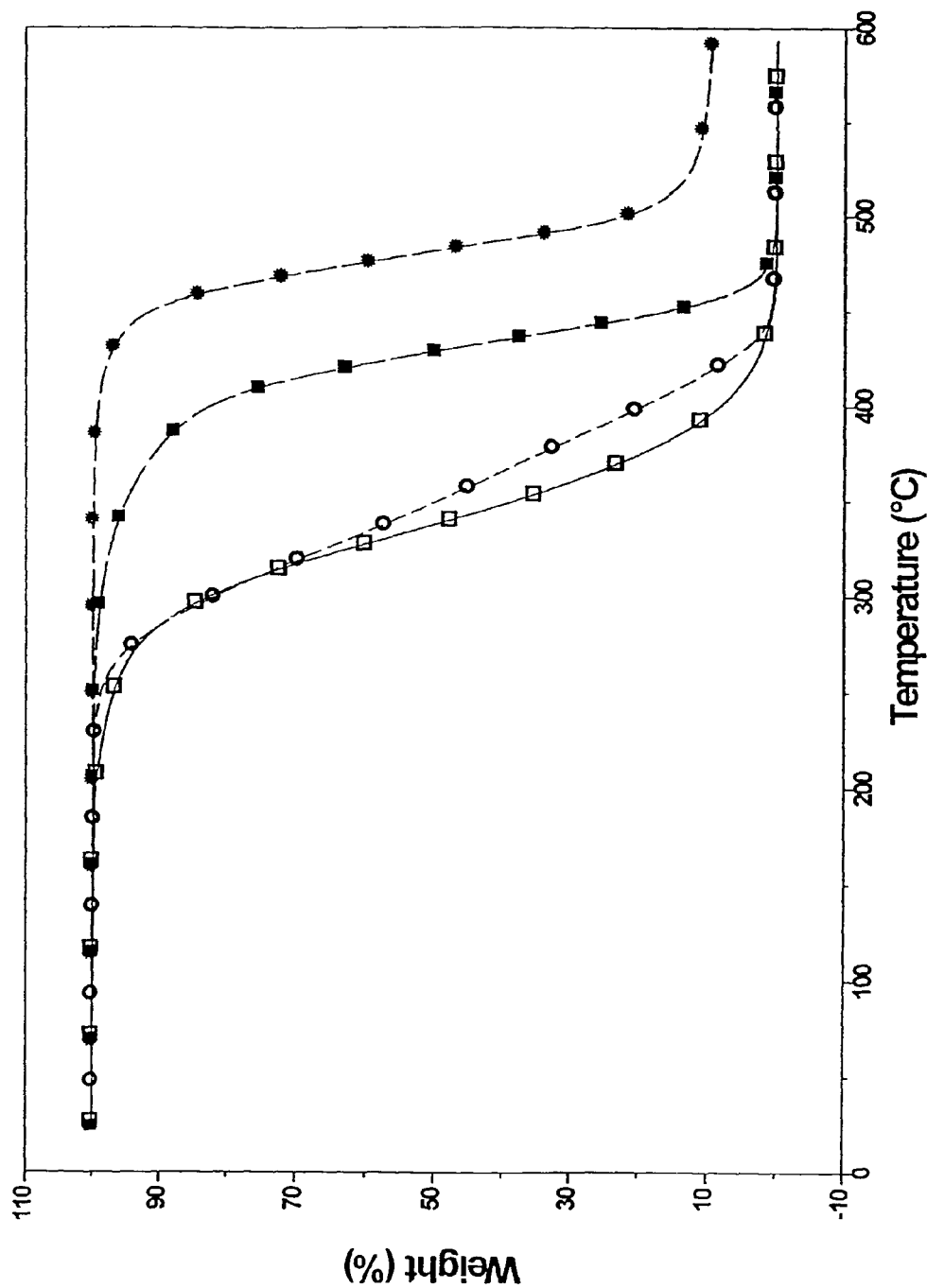
FIG. 3 depicts a TGA curve of cured reaction products of compositions based on limonene diepoxide (square), Compound XVI of U.S. Pat. Nos. 5,948,922 (Ober) and 5,973,033 (Ober)(circle), commercially available diepoxidized dicycloaliphatic ester (ERL 4221)(closed square) and commercially available diglycidyl ether of bisphenol F epoxy resin (RE-404-S)(asterisk), cured with an anhydride curing agent.
Figure 4:
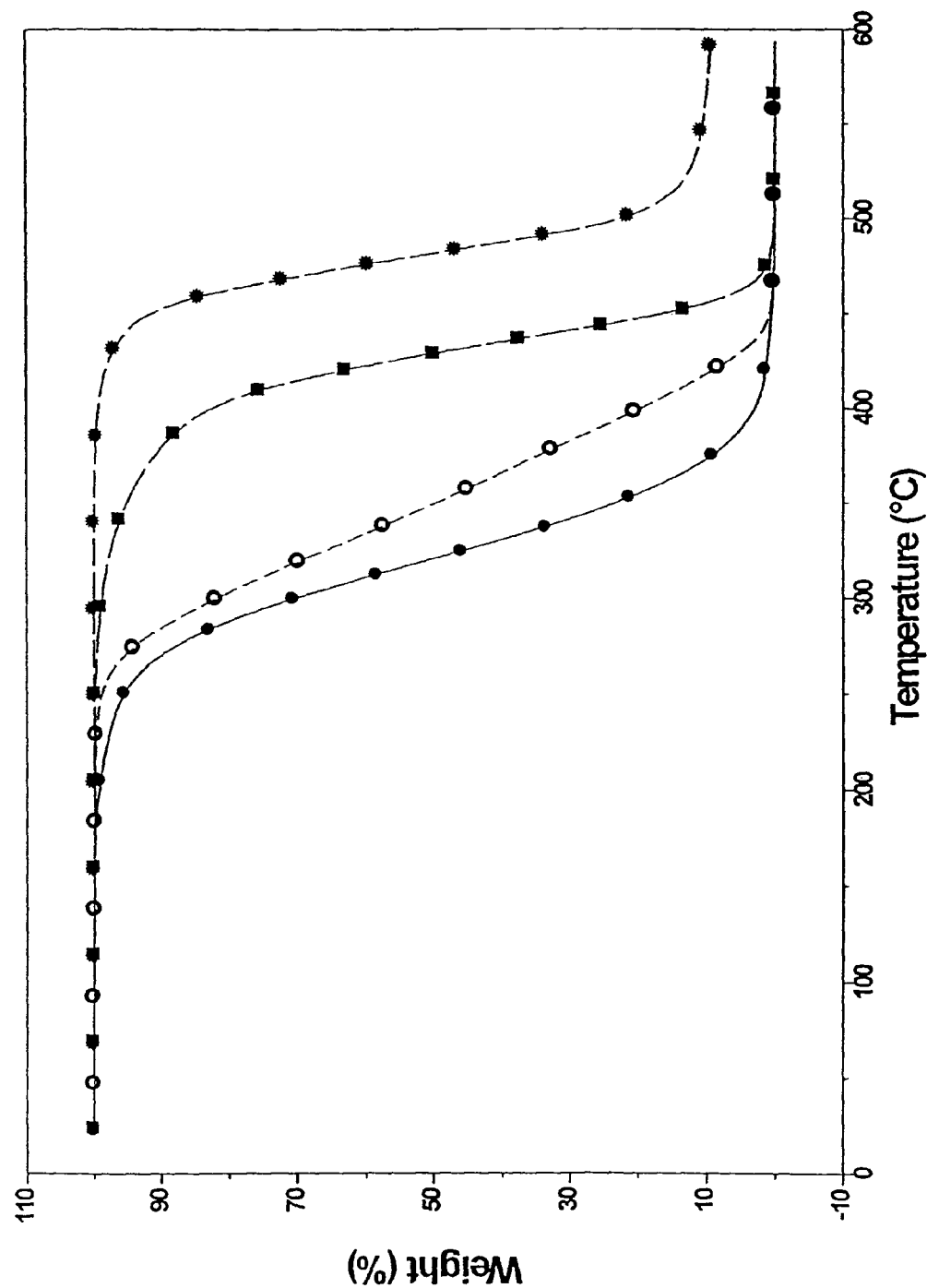
FIG. 4 depicts a TGA curve of cured reaction products of compositions based on terpinene diepoxide (square), Compound XVI of the '922 and '033 patents (circle), ERL 4221 (closed square) and RE-404-S (asterisk), cured with an anhydride curing agent.

Reference to FIGS. 3-4 show TGA data for cured reaction products of Sample Nos. 1-5 using an anhydride curing agent, compared with TGA data for cured reaction products of compositions based on the commercially available epoxies ERL-4221 (Sample No. 4) and RE-404-S (Sample No. 5), and Compound XVI of the '922 and '033 patents (Sample No. 3).

Figure 5:
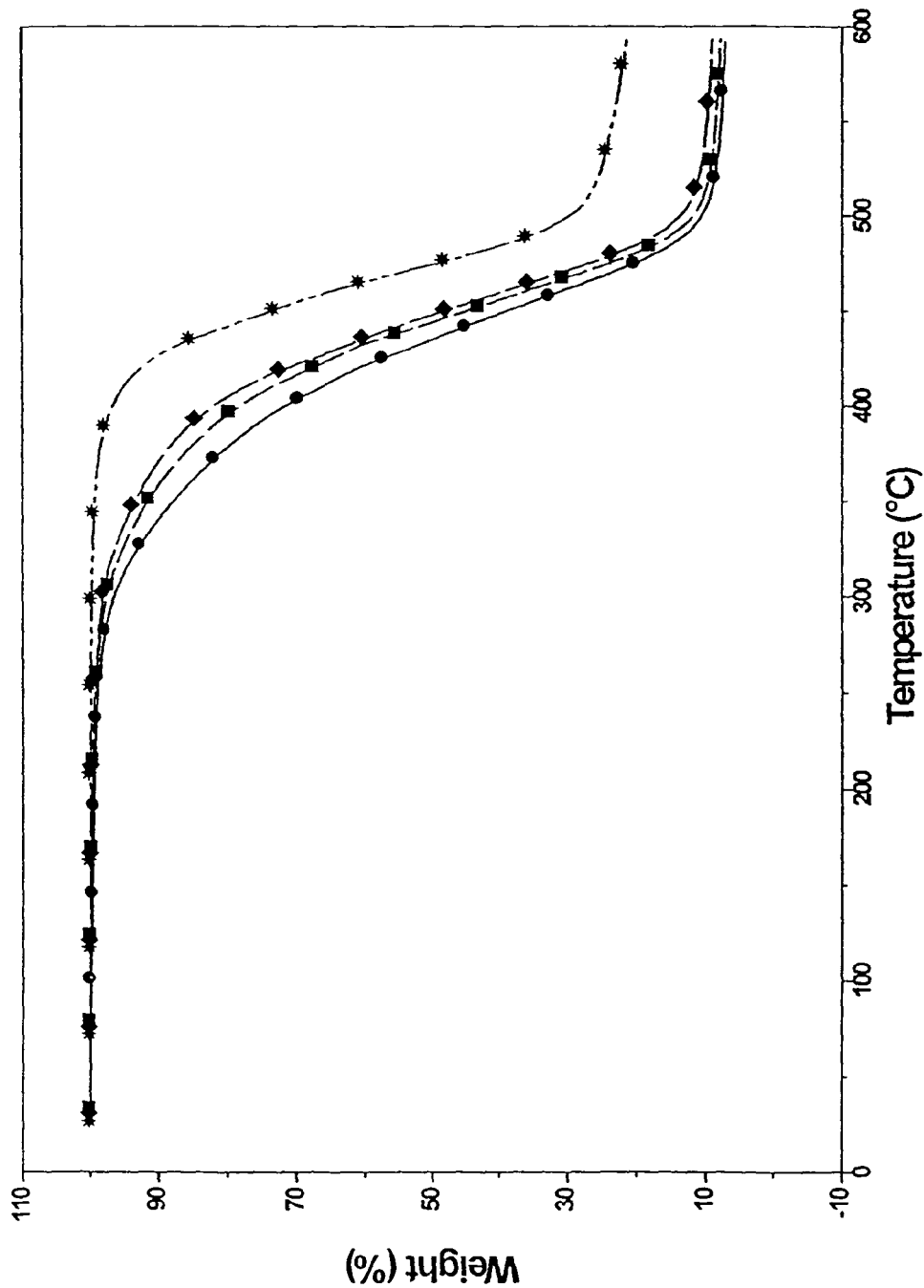
FIG. 5 depicts a TGA curve of cured reaction products of compositions based on limonene diepoxide and RE-404-S at different ratios, and RE-404-S (asterisk), cured with an imidazole/dicyandiamide curing agent.
Figure 6:
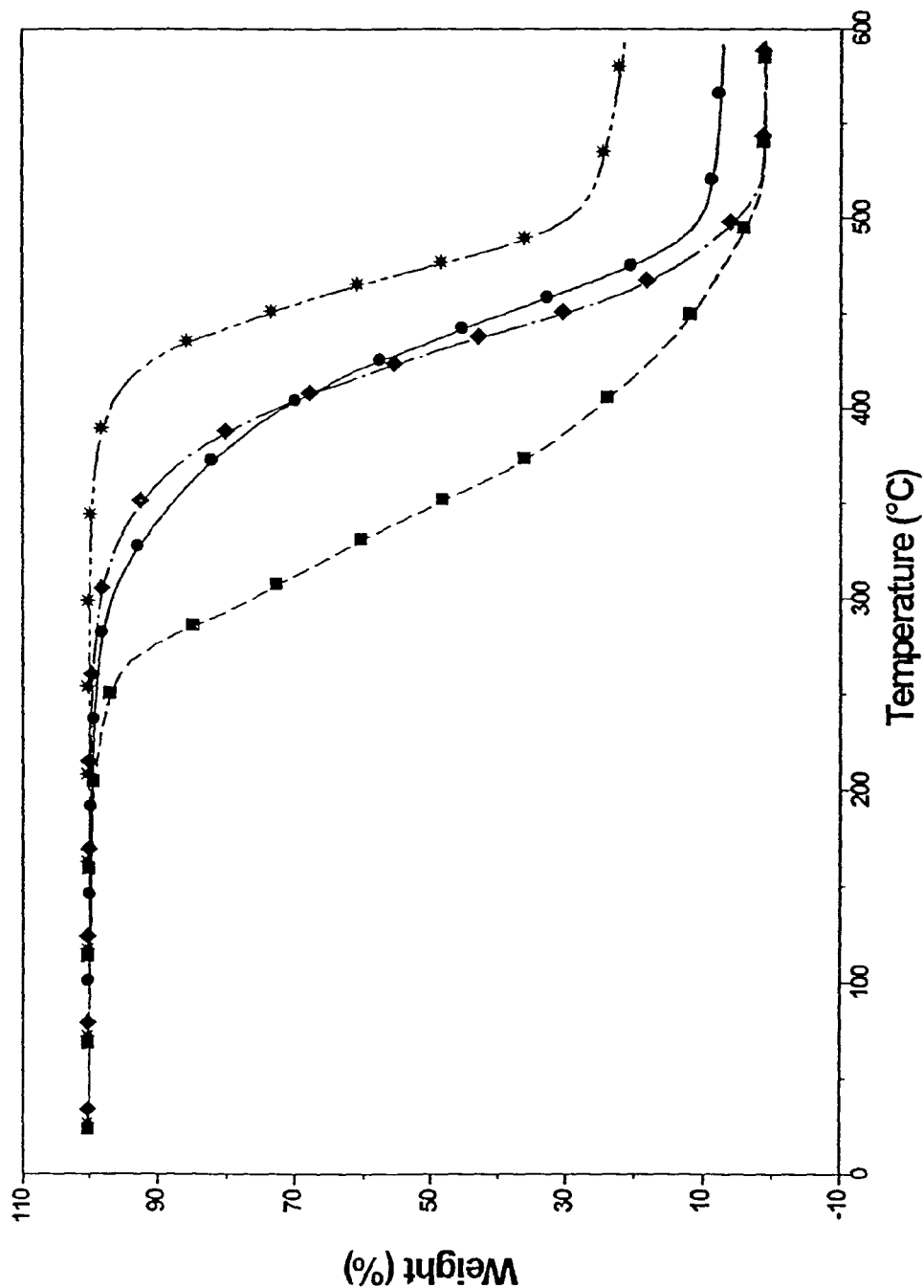
FIG. 6 depicts a TGA curve of cured reaction products of compositions based on limonene diepoxide/RE-404-S (circle), Compound XVI of the '922 and '033 patents (square), ERL 4221 (diamond) and RE-404-S (asterisk), cured with an imidazole/dicyandiamide curing agent.

Reference to FIGS. 5-6 show TGA data for cured reaction products of Sample Nos. 7-10 using an imidazole/dicyandiamide curing agent, compared with TGA data for cured reaction products of compositions based on the commercially available epoxies ERL-4221 (Sample No. 9), and RE-404-S (Sample No. 10), and Compound XVI of the '922 and '033 patents (Sample No. 8).

Figure 7:
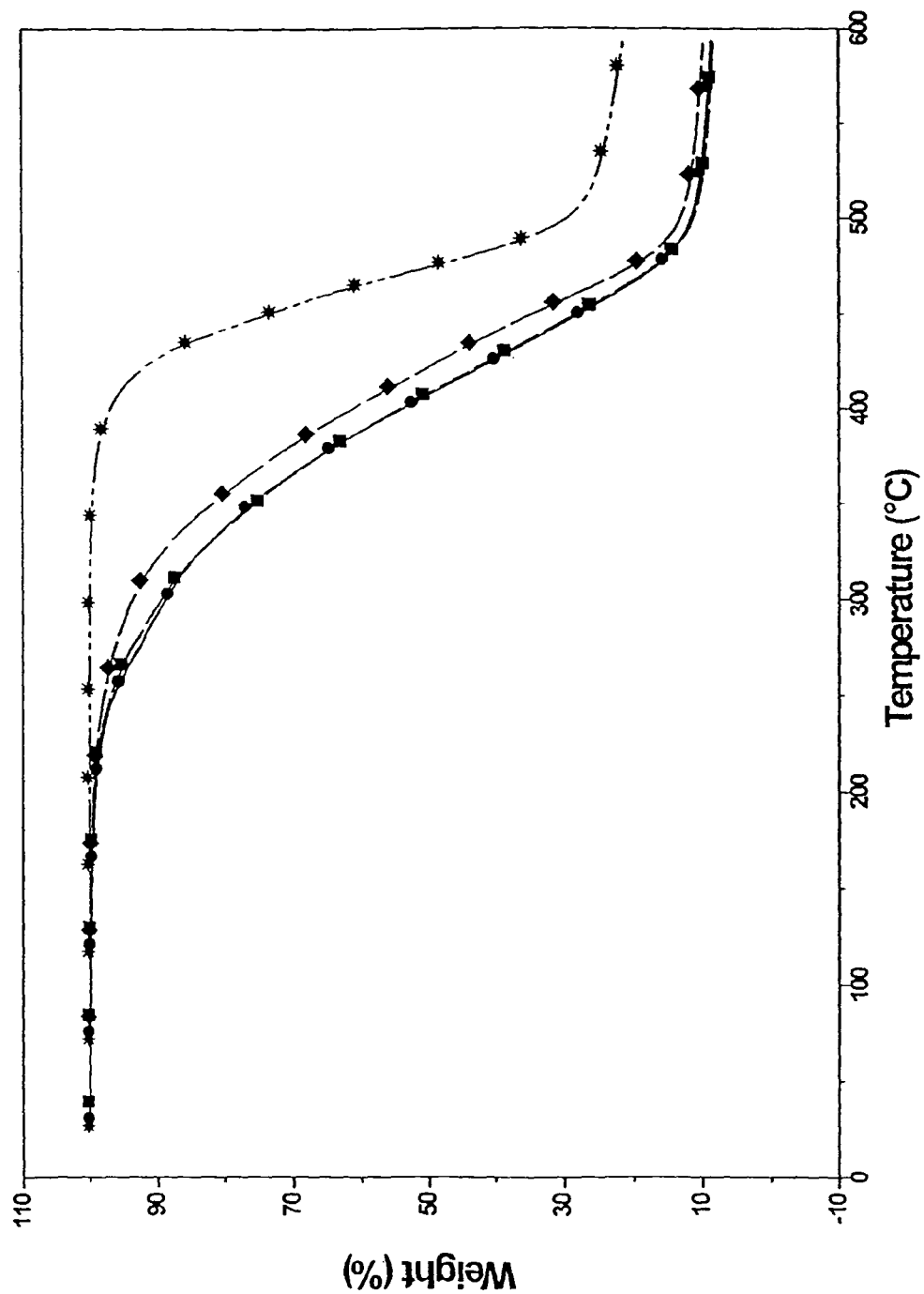
FIG. 7 depicts a TGA curve of cured reaction products of compositions based on gamma-terpinene diepoxide and RE-404-S at different ratios, and RE-404-S (asterisk), cured with an imidazole/dicyandiamide curing agent.
Figure 8:
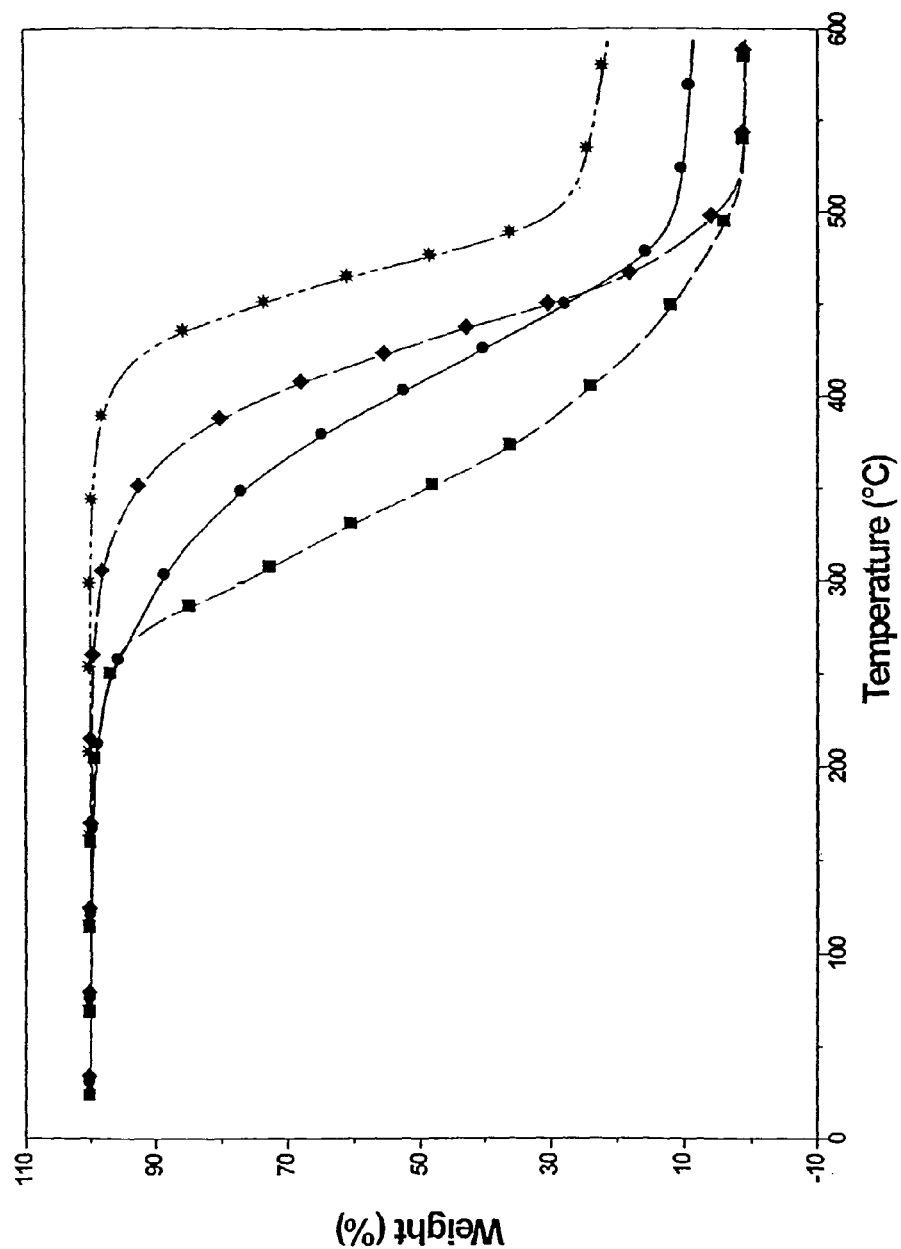
FIG. 8 depicts a TGA curve of cured reaction products of compositions based on gamma-terpinene diepoxide/RE-404-S (circle), Compound XVI of the '922 and '033 patents (square), ERL 4221 (diamond) and RE-404-S, cured with an imidazole/dicyandiamide curing agent.

Reference to FIGS. 7-8 show TGA date for cured reaction products of Sample Nos. 10 and 11-16 using an imidazole/dicyandiamide curing agent, comparing TGA data for cured reaction products of compositions based on the commercially available RE-404-S, and cured reaction products of 80:20, 70:30, and 60:40 combinations of limonene diepoxide/RE-404-S (Sample Nos. 11-13) and of terpinene diepoxide (Samples Nos. 14-16).

Figure 9:
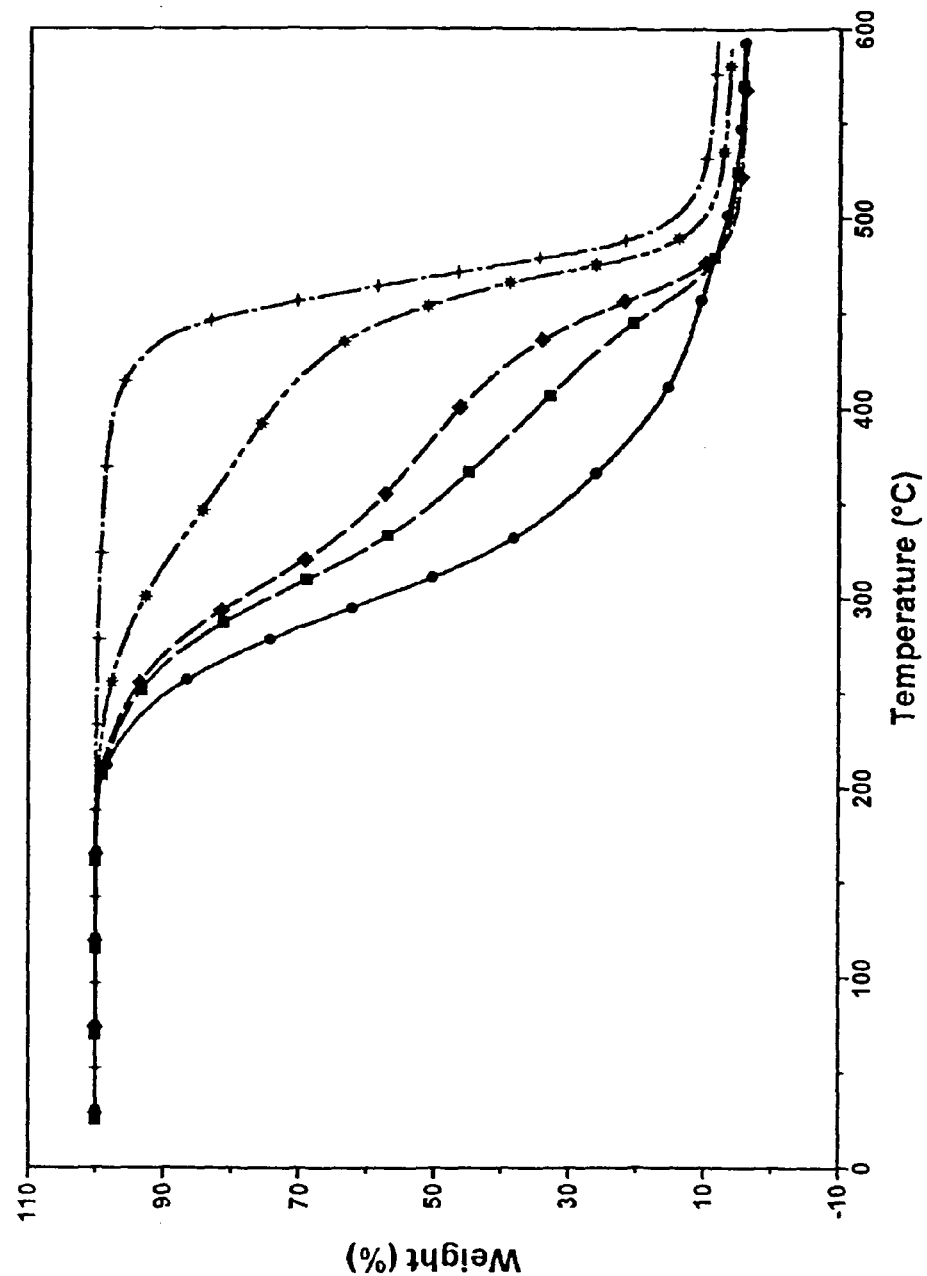
FIG. 9 depicts a TGA curve of cured reaction products of compositions based on methyl cyclopentadiene dimer diepoxide and RE-404-S at different ratios, and RE-404-S (asterisk), cured with an anhydride curing agent.
Figure 10:
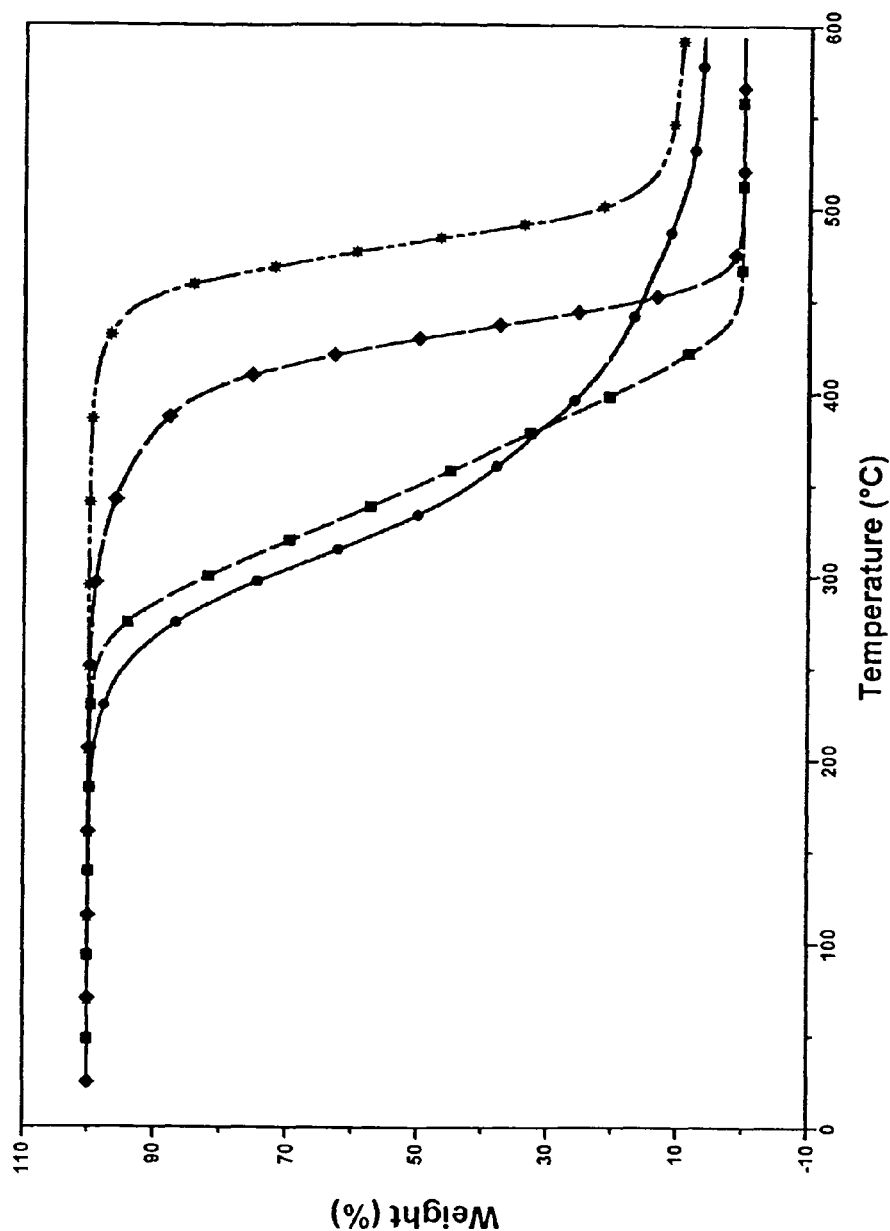
FIG. 10 depicts a TGA curve of cured reaction products of compositions based on methyl cyclopentadiene dimer diepoxide (circle), Compound XVI of the '922 and '033 patents (square), ERL 4221 (diamond) and RE-404-S (asterisk), cured with an anhydride curing agent.

Reference to FIG. 9-10 sow TGA data for anhydride cured reaction products of Sample Nos. 5 (RE-404-S), 32 (methyl cyclopentadiene dimer diepoxide), and 50-52. having 80:20, 60:40 and 40:60 combinations of methyl cyclopentadiene dimer diepoxide/RE-404-S and RE-404-S, and for anhydride cured reaction products of methyl cyclopentadiene dimer diepoxide (Sample No. 4) and RE-404-S (Sample No. 5), and Compound XVI of the '922 and '033 patents (Sample No. 3).

Figure 11:
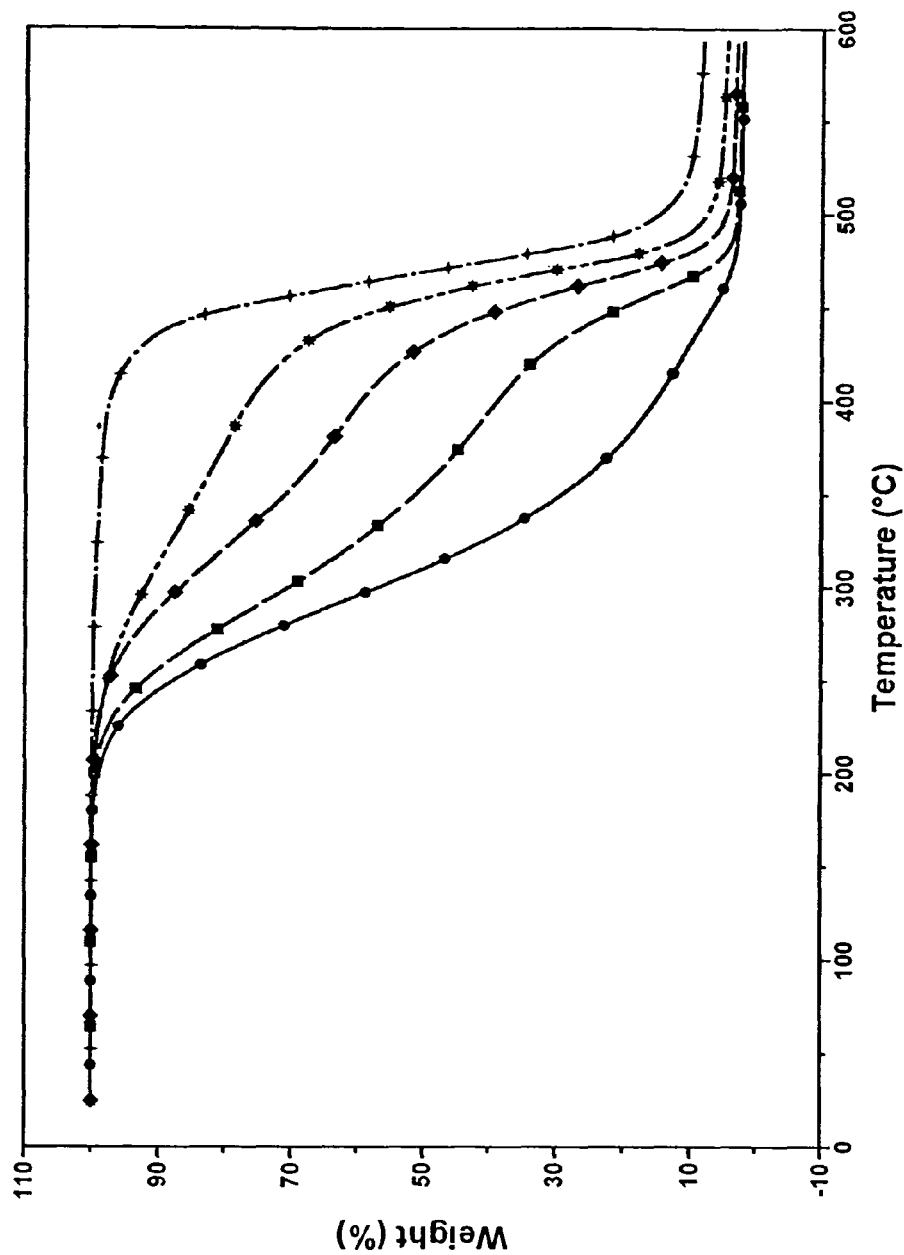
FIG. 11 depicts a TGA curve of cured reaction products of compositions based on ethylidene norbornene diepoxide and RE-404-S at different ratios, and RE-404-S (asterisk), cured with an anhydride curing agent.
Figure 12:
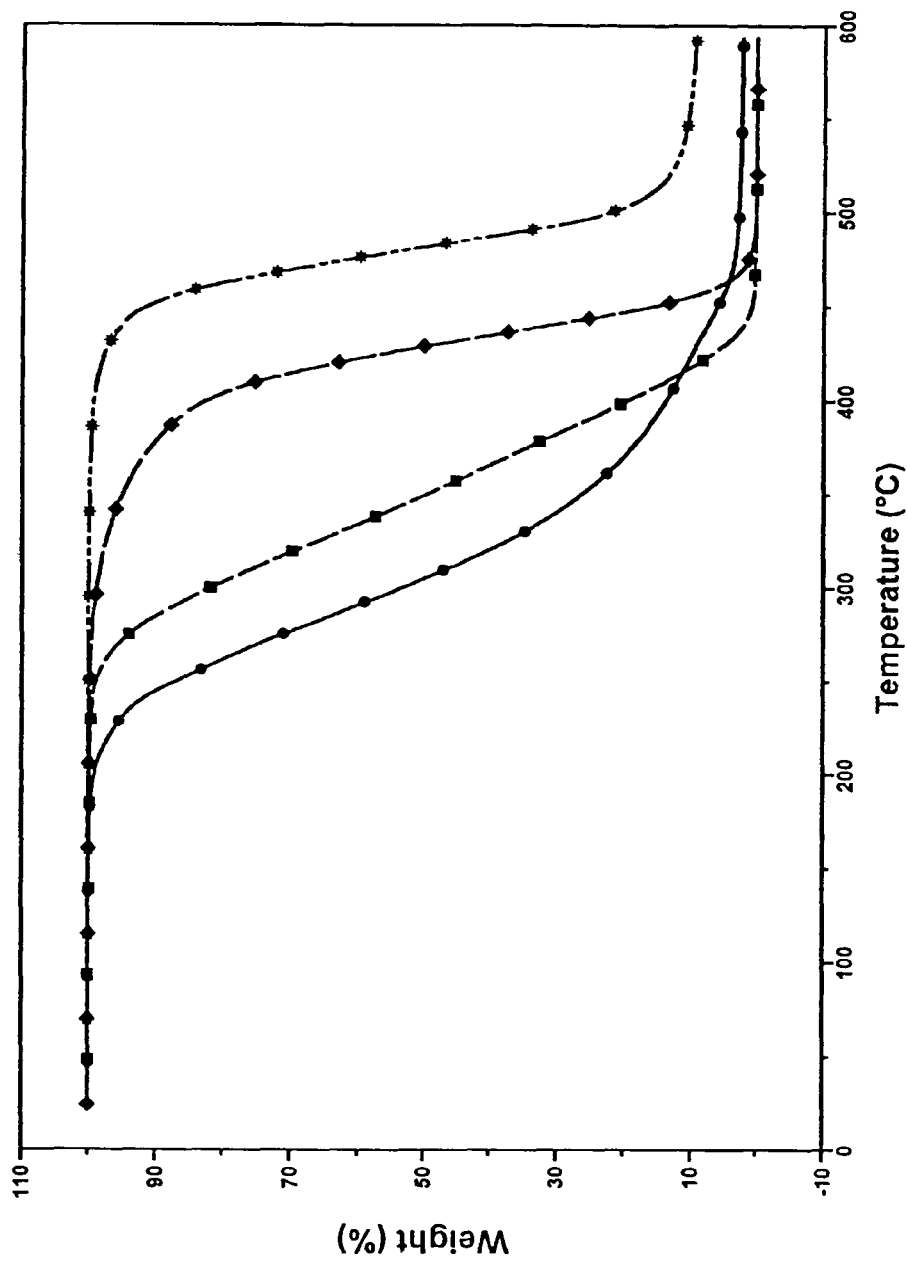
FIG. 12 depicts a TGA curve of cured reaction products of compositions based on ethylidene norbornene diepoxide (circle), Compound XVI of the '922 and '033 patents (square), ERL 4221 (diamond) and RE-404-S, cured with an anhydride curing agent.

Reference to FIGS. 11-12 show TGA data for anhydride cured reaction products of Sample Nos. 5, 31 (ethylidene norbornene dieproxide), 53-55, having 80:20, 60:40 and 40:60 combinations of ethylidene norbornene diepoxide/RE-404-S, and RE-404-S, and anhydride cured reaction products of ethylidene norbornene dieproxide (Sample No. 4) and RE-404-S (Sample No. 5), and Compound XVI of the '922 and '033 patents (Sample No. 3).

Figure 13:
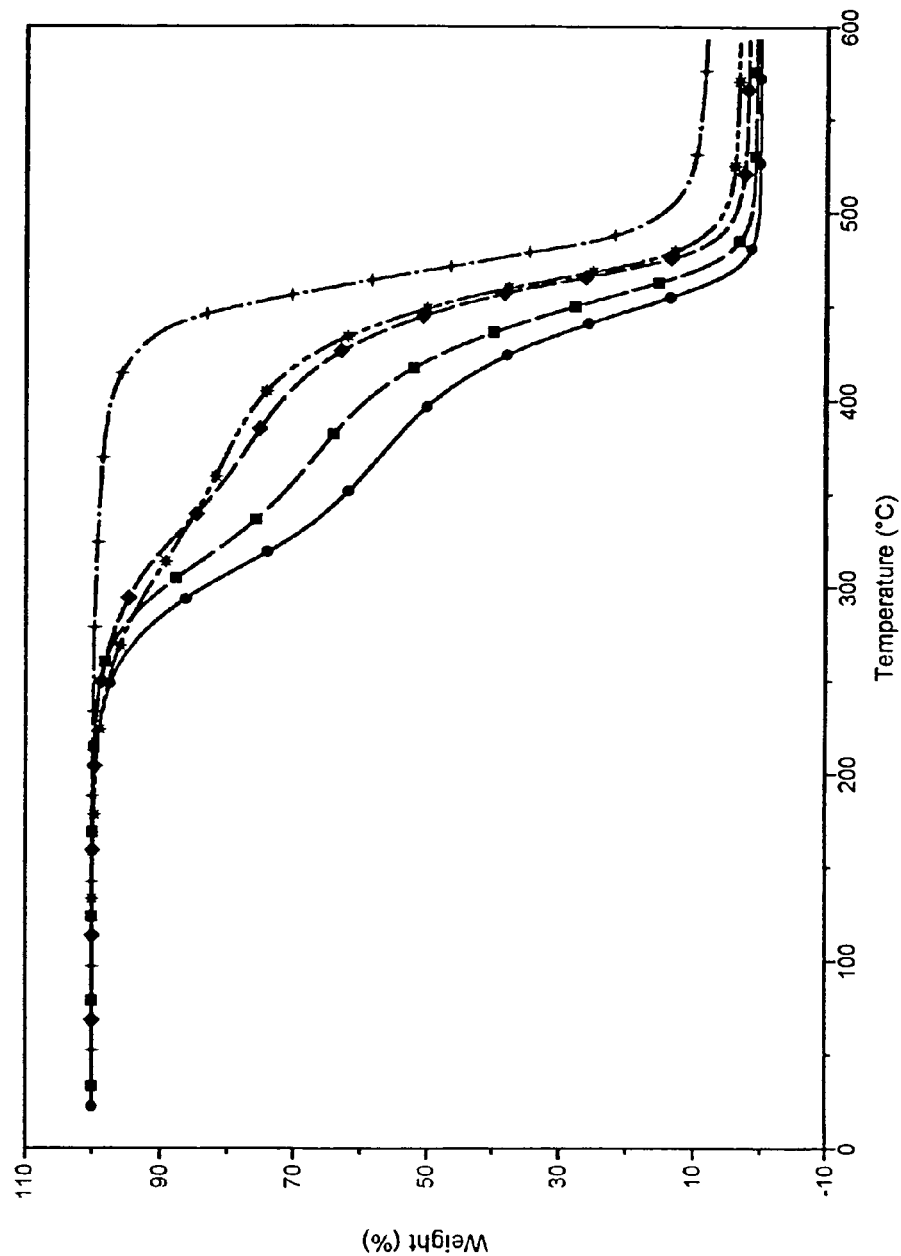
FIG. 13 depicts a TGA curve of cured reaction products of compositions based on nopol epoxide glycidyl ether and RE-404-S at different ratios, and RE-404-S (asterisk), cured with an anhydride curing agent.
Figure 14:
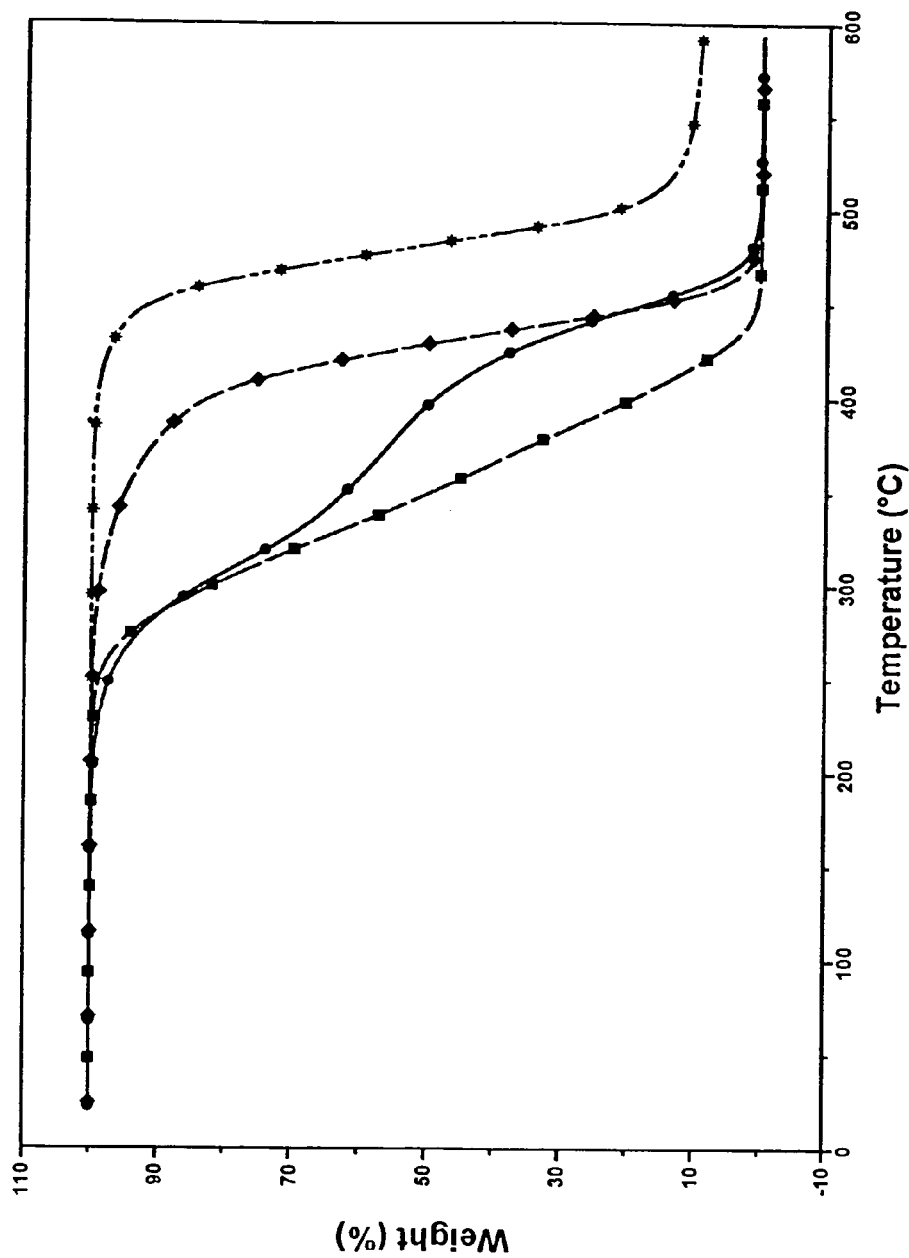
FIG. 14 depicts a TGA curve of cured reaction products of compositions based on nopol epoxide glycidyl ether (circle), Compound XVI of the '922 and '033 patents (square), ERL 4221 (diamond) and RE-404-S, cured with an anhydride curing agent.

Reference to FIGS. 13-14 show TGA data for anhydride cured reaction products of Sample Nos. 5, 55-58 and 59 (nopol epoxide glycidyl ether), having 80:20, 60:40, and 40:60 combinations of nopol epoxide glycidyl ether/RE-404-S, and RE-404-S, and anhydride cured reaction products of nopol epoxide glycidyl ether (Sample No. 59), commercially available epoxies ERL-4221 (Sample No. 4), and RE-404-S (Sample No. 5) and Compound XVI of the '922 and '033 patents (Sample Nos. 3).

The TGA data indicate that cured reaction products of the inventive compositions (e.g., Sample Nos. 1-2, and 7-8) degrade and lose mass at a temperature lower than cured reaction products of the compositions based on either of the commercially available epoxies, to which reference is made above.

Practical reworkability was demonstrated using a hot air generator to heat the area around the die, fixed to the circuit board with the compositions of Sample Nos. 17-25, 42-46 and 49, to an air temperature of about 280° C., with a die temperature of about 215-220° C. for a period of time of about 1 to about 2 minutes. Then, the die may be easily removed by pulling or twisting the die from the circuit board using tweezers in a period of time of about 20 to about 30 seconds. The circuit board may then be cleaned using a dremel at about 25,000 rpm, followed by application of a flat-end horse hair brush. The circuit board cleaning ordinarily occurs within a period of time of about 2 to about 3 minutes.

In addition, Sample Nos. 26-30 were reworked by localized heating to a temperature of about 100° C. for a period of time of about 60 minutes. Although reworkability data for these samples was observed, an increased temperature for a shortened time period would likely improve the data observed.

Thermosetting resin compositions prepared without limonene diepoxide, with the balance of the epoxy resin component from the RE-404-S epoxy resin (e.g., Sample Nos. 5 or 10), which was dispensed and cured as above, do not allow for die removal in the manner so described.

The site of the failed semiconductor chip should then be fluxed and a new semiconductor chip may be attached using conventional flip chip technology. Then, the thermosetting resin composition of this invention may be applied around the periphery of the newly-replaced semi-conductor chip and cured by heating to an appropriate temperature, as described herein.

The samples described above are presented as illustrative, rather than limiting, examples of the inventive compositions. Many additional embodiments thereof are included in the spirit and scope of the invention, which is defined by the claims.

What is claimed is:

1. A compound within the following structure:

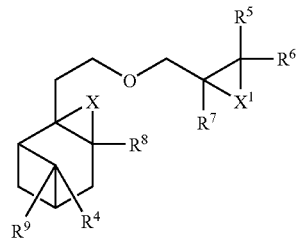

wherein $R^4$, $R^5$, $R^6$, $R^7$, $R^8$, and $R^9$ are individually selected from the group consisting of hydrogen, alkyl from one to eight carbon atoms, alkenyl from two to eight carbon atoms and combinations thereof, and X and $X^1$ may be selected from the group consisting of O and S.

2. A compound represented by:

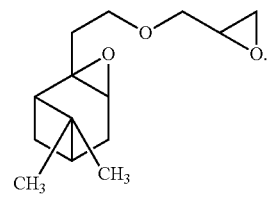

* * * * *